US006951651B2

(12) United States Patent
Diamond

(10) Patent No.: US 6,951,651 B2
(45) Date of Patent: Oct. 4, 2005

(54) CTL EPITOPE ANALOGS

(75) Inventor: Don J. Diamond, Glendora, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 10/643,888

(22) Filed: Aug. 20, 2003

(65) Prior Publication Data

US 2004/0086520 A1 May 6, 2004

Related U.S. Application Data

(62) Division of application No. 09/692,325, filed on Oct. 20, 2003, now Pat. No. 6,632,435.
(60) Provisional application No. 60/187,871, filed on Mar. 8, 2000, and provisional application No. 60/160,633, filed on Oct. 20, 1999.

(51) Int. Cl.[7] .................. A61K 39/245; A61K 39/25; A61K 39/12; A61K 38/00; A61K 39/38
(52) U.S. Cl. ............................ 424/230.1; 424/184.1; 424/185.1; 424/186.1; 424/204.1; 424/689; 424/690; 424/698; 514/2; 514/15; 530/300; 530/328
(58) Field of Search ..................... 424/230.1, 184.1, 424/185.1, 186.1, 204.1, 689, 690, 698, 231.1; 514/2, 15, 44; 530/300, 328

(56) References Cited

U.S. PATENT DOCUMENTS

| | | | |
|---|---|---|---|
| 4,689,225 A | | 8/1987 | Pereira |
| 5,248,768 A | | 9/1993 | Lussenhop et al. |
| 5,405,940 A | | 4/1995 | Boon et al. |
| 5,635,363 A | | 6/1997 | Altman et al. |
| 6,074,645 A | | 6/2000 | Diamond et al. |
| 6,156,317 A | * | 12/2000 | Diamond et al. ........ 424/186.1 |
| 6,251,399 B1 | * | 6/2001 | Diamond et al. ........ 424/186.1 |
| 6,544,521 B2 | * | 4/2003 | Diamond ................. 424/186.1 |
| 6,562,345 B1 | * | 5/2003 | Diamond ................. 424/186.1 |
| 6,632,435 B1 | * | 10/2003 | Diamond ................. 424/186.1 |
| 6,726,910 B2 | * | 4/2004 | Diamond ................. 424/186.1 |
| 6,727,093 B2 | * | 4/2004 | Diamond ................... 435/325 |
| 6,733,973 B2 | * | 5/2004 | Diamond ....................... 435/6 |
| 6,843,992 B2 | * | 1/2005 | Diamond ................. 424/186.1 |
| 2002/0146820 A1 | * | 10/2002 | Diamond ................. 435/320.1 |
| 2003/0118602 A1 | * | 6/2003 | Diamond ................. 424/186.1 |
| 2003/0190328 A1 | * | 10/2003 | Diamond ................. 424/204.1 |
| 2003/0224980 A1 | * | 12/2003 | Diamond ..................... 514/12 |
| 2004/0086520 A1 | * | 5/2004 | Diamond ................. 424/185.1 |
| 2004/0101534 A1 | * | 5/2004 | Diamond ................. 424/186.1 |
| 2004/0161843 A1 | * | 8/2004 | Diamond ..................... 435/372 |
| 2004/0209314 A1 | | 10/2004 | Lang et al. |
| 2004/0265325 A1 | * | 12/2004 | Diamond et al. ........ 424/186.1 |

FOREIGN PATENT DOCUMENTS

WO    PCT 94/00150    1/1994

OTHER PUBLICATIONS

Zala et al, Hematology, 2000, pp. 339–355.*
Diamond et al, Blood, 1997, 90/5:1751–1767.*
Prosch et al, biol. Chem. Hoppe–Seyler, 1996, 377:195–201.*
Corr et al, Methods in Microbiology, 2002, 32:527–550.*
Lore et al, J. Immunology, 2003, 171:4320–4328.*
Temperton et al, J. Medical Virology, 2003, 70:86–90.*
Endresz et al, Vaccine, 2001, 19:3972–3980.*
Benmohamed et al, Immunology, 2002, 106:113–121.*
Andersson et al, Current Opinion in Immunology, 2002, 14:409–412.*
Alexander et al., "Development of High Potency Universal DR–Restricted Helper Epitopes by Modification of High Affinity DR–Blocking Peptides," Immunity 1:751–761, Dec. 1994.
Borysiewicz et al., "Human Cytomegalovirus–Specific Cytotoxic T Cells," J. Exp. Med 168:919–931, Sep. 1988.
Brouwenstijn et al., "Definition if Unique and Shared T–Cell Defined Tumor Antigens in Human Renal Cell Carcinoma," Journal of Immunotherapy 21(6):427–434, 1998.
Carruth et al., "An Algorithm for Evaluating Human Cytotoxic t Lymphocyte Responses to Candidate AIDS Vaccines," Aids Research and Human Retroviruses 15(11):1021–1034, 1999.
Chujoh et al., "The role of anchor residues in the binding of peptides to HLA–A*1101 molecules," Tissue Antigens 52:501–509, 1998.
D'Amaro et al., "A Computer Program for Predicting Possible Cytotoxic T Lymphoctye Epitopes Based on HLA Class I Peptide–Binding Motifs," Human Immunology 43:13–18, 1995.
Del Val et al., "Efficient Processing of an Antigenic Sequence for Presentation by MHC Class I Molecules Depends on its Neighboring Residues in the Protein," Cell 66:1145–1153, Sep. 20, 1991.
Del Val et al., "Protection Against Lethal Cytomegalovirus Infection by a Recombinant Vaccine Containing a Single Nonameric T–Cell Epitope," Journal of Virology 65(7):3641–3646, Jul. 1991.
Diamond et al., "Development of a Candidate HLA A*0201 Restricted Peptide–Based Vacicne Against Human Cytomegalovirus Infection," Blood 90(5):1751–1767, Sep. 1, 1997.
Drijfhout et al., "Detailed Motifs for peptide Binding to HLA–A*0201 Derived from Large Random Sets of Peptides Using a Cellular Binding Assay," Human Immunology 43:1–12, 1995.

(Continued)

Primary Examiner—N. M. Minnifield
(74) Attorney, Agent, or Firm—Rothwell, Figg, Ernst & Manbeck p.c.

(57) ABSTRACT

We have screened the HCMV-specific T cell clone, 33F4, with a nonamer PS-SCL based on SEQ ID NO: 1, and described a series of analog peptides that are recognized with greater affinity than the native peptide sequence.

8 Claims, 10 Drawing Sheets

OTHER PUBLICATIONS

Ellis et al., Chapter 29, "New Technologies for Making Vaccines", pp. 568–575.

Falk et al., "Allele–specific motifs revealed by sequencing of self–peptides eluted from MHC molecules," Nature 351:290–296, May 23, 1991.

Fremont et al., "Crystal Structures of Two Viral Peptides in Complex with Murine MHC Class I H–2$K^b$," Science 257:919–927, Aug. 14, 1992.

Gönczöl et al., "Preclinical evaluation of an ALVAC (canarypox)–human cytomegalovirus glycoprotein B vaccine candidate," Vaccine 13(12):1080–1085, 1995.

Greenberg et al., "Development of a Treatment Regimen for Human Cytomegalovirus (CMV) Infection in Bone Marrow Transplantation Recipients by Adoptive Transfer of Donor–Derived CMV–Specific T Cell Clones Expanded in Vitro," Annals of the New York Academy of Sciences (Antigen and Clone–Specific Immunoregulation) 636:184–195, 1991.

Gundlach et al., "Specificity and Degeneracy of Minor Histocompatibility Antigen–Specific MHC–Restricted CTL," J. Immunol. 156:3645–3651, 1996.

Hemmer et al., "Cutting Edge: Predictable TCR Antigen Recognition Based on Peptide Scans Leads to the Identification of Agonist Ligands with No Sequence Homology," J. Immunology 160:3631–3636, 1998.

Kawashima et al., "The Multi–epitope Approach for Immunotherapy for Cancer: Identification of Several CTL Epitopes from Various Tumor–Associated Antigens Expressed on Solid Epithelial Tumors," Human Immunology 59:1–14, 1998.

Khattab et al., "Three T–Cell Epitopes Within the C–Terminal 265 Amino Acids of the Matrix Protein pp65 of Human Cytomegalovirus Recognized by Human Lymphocytes," J. Med. Virol. 52:68–76, 1997.

Larosa et al., "Development of In Vitro Stimulation (IVS) Protocol to Measure CMV Specific CTL Activity Using HLA–Restricted Specific CtL Epitopes,",Blood 92(10 – suppl. 1):518a, 1998 (Abstract 2129).

Leggatt et al., "The Importance of Pairwise Interactions Between Peptide Residues in the Delineation of TCR Specificity," J. Immunology 161:4728–4735, 1998.

Lipford et al., "Peptide engineering allows cytotoxic T–cell vaccination against human papilloma virus tumour antigen, E6," Immunology 84:298–303, 1995.

Madden et al., "The Antigenic Identity of Peptide–MHC Complexes: A Comparison of the Conformations of Five Viral Peptides Presented by HLA–A2," Cell 75:693–708, Nov. 19, 1993.

McLaughlin–Taylor et al., "Identification of the Major Late Human Cytomegalovirus Matrix Protein pp65 as a Target Antigen for $CD8^+$ Virus–Specific Cytotoxic T Lymphocytes," J. Med. Virol. 43:103–110, 1994.

Nijman et al., "Identification of peptide sequences that potentially trigger HLA–A2.1–restricted cytotoxic T lymphocytes," Eur. J. Immunol. 23:1215–1219, 1993.

Ono et al., "Alterations in TCR–MHC Contacts Subsequent to Cross–Recognition of Class I MHC and Singly Substituted Peptide Variants," J. Immunol. 161:5454–5463 (1998).

Oseroff et al., "Pools of lipidated HTL–CTL construct prime for multiple HBV and HCV CTL eptiope responses," Vaccine 16(8):823–833, 1998.

Pande et al., "Human Cytomegalovirus Strain Towne pp65 gene: Nucleotide Sequence and Expression in *Escherichia coli,*" Virology 182:220–228, 1991.

Parkhurst et al., "Improved Induction of Melanoma–Reactive CTL with Peptides from the Melanoma Antigen gp100 Modified at HLA–A*0201–Binding Resiudes," J. Immunol. 157:2539–2548, 1996.

Rammensee et al., "MHC ligands and peptide motifs: first listing," Immunogenetics 41:178–228, 1995.

Rammensee et al., "Peptide Naturally Presented by MHC Class I Molecules," Annu. Rev. Immunol. 11:213–44, 1993.

Rasmussen, "Immune Response to Human Cytomegalovirus Infection," Current Topics in Microbiology and Immunology 154:222–254, 1990.

Schulz et al., "Peptide–induced antiviral protection by cytotoxic T cells," Proc. Natl. Acad. Sci. USA 88:991–993, Feb. 1991.

Sette et al., "Peptide Binding to the Most Frequent HLA–A Class I Alleles Measured by Quantitative Molecular Binding Assays," Molecular Immunol. 31(11):813–822, 1994.

Sette et al., "The Relationship Between Class I Binding Affinity and Immunogenicity of Potential Cytotoxic T Cell Epitopes," J. Immunol. 153:5586–5592, 1994.

Valmori et al., "Diversity of the Fine Specificity Displayed by HLA–A*0201–Restricted CTL Specific for the Immunodominant Melan–A/Mart–1 Antigenic Peptide," J. Immunol. 161:6956–6962, 1998.

Vierboom et al., "Peptide Vaccination with an Anchor–Replaced CTL Epitope Protects Against Human Papillomarivus Type 16–Induced Tumors Expressing the Wild–Type Epitope," J. Immunotherapy 21(6):399–408, 1998.

Wentworth et al., "In Vitro Induction of Primary, Antigen–Specific CTL From Human Peripheral Blood Mononuclear Cells Stimulated with Synthetic Peptides," Molecular Immunology 32(9):603–612, 1995.

Wills et al., "The Human Cytotoxic T–Lymphocyte (CTL) Response to Cytomegalovirus is Dominated by Structural Protein pp65: Frequency, Specificity, and T–Cell Receptor Usage of pp65–Specific CTL," J. of Virol. 70(11):7569–7579, Nov. 1996.

Wilson et al., "Immunogenicity. I. Use of Peptide Libraries to identify Epitopes that Activate Clonotypic $CD4^+$ T Cells and induce T Cell Responses to Native peptide Ligands," J. Immunol. 163:6424–6434, 1999.

Zeh III et al., "Flow–Cytometric Determination of Peptide––Class I Complex Formation Identification of p53 Peptides That Bind to HLA–A2," Human Immunology 39:79–86, 1994.

Hemmer et al., "The Use of Soluble Synthetic Peptide Combinatorial Libraries to Determine Antigen Recognition of T Cells," *J. Peptide Res.,* 52:338–345, 1998.

Hiemstra et al., "Definition of Natural T Cell Antigens With Mimicry Epitopes Obtained From Dedicated Synthetic Peptide Libraries[1],", *J Immunol.,* 161:4078–4082, 1998.

Blake et al., "Use of Combinatorial Peptide Libraries to Construct Functional Mimics of Tumor Epitopes Recognized By MHC Class . . . ," *J. Exp. Med.,* 184:121–130, 1996.

Pinilla et al., "Rapid Identification of High Affinity Peptide Ligands Using Positional Scanning . . . ," *BioTechniques,* 13(6):901–905, 1992.

Sandberg et al., "Recognition of the Major Histocompatibility Complex . . . ," *J. Exp. Med.,* 189 (6):883–893, 1999.

Soares et al., "Differential Activation of T Cells by Natural Antigen Peptide Analogues . . . ," *The Journal of Immun.,* 160:4768–4775, 1998.

Udaka et al., "Decrypting the Structure of Major Histocompatibility Complex . . . ," *J. Exp. Med.,* 181:2097–2108, 1995.

Gratama et al., "Diagnostic Potential of Tetramer–based Monitoring of Cytomegalovirus–specific CD8+ T Lymphocytes in Allogeneic Stem Cell Transplantation," *Clinical Immunology* 106:29–35, 2003.

Engstrand et al., "Characterization of CMV pp65–specific CD8+ T Lymphocytes Using MHC Tetramers in Kidney Transplant Patients and Healthy Participants," *Transplantation* 69(11):2243–2250, 2000.

Cwynarski et al., "Direct Visualization of Cytomegalovirus–Specific T Cell Reconstitution After Allogeneic Stem Cell Transplantation," *Blood* 97(5):1232–1240, 2001.

Einsele et al., "Infusion of Cytomegalovirus (CMV)–specific T Cells for the Treatment of CMV Infection Not Responding to Antiviral Chemotherapy," *Blood* 99(11):3916–3922, 2002.

Moss et al., "Direct Adoptive Transfer of Donor Cytomegalovirus–specific CTL To Transplant Patients Following Selection by HLA–Peptide Tetramers," *12$^{th}$ Int'l. Cong. Immunol.* Montreal, Canada (2004).

Aubert et al., "Cytomegalovirus–Specific Cellular Immune–Responses and Viremia in Recipients of Allogeneic Stem Cell Transplants," J. Infect. Dis., 184:955–963, 2001.

Gratama et al., "Tetramer–Based Quantification of Cytomegalovirus (CMV)–Specific CD8+ T Lymphocytes in T–Cell Depleted Stem Cell Grafts and After Transplantation May Identify Patients At Risk For Progressive CMV Infection," *Blood* 98(5):1358–1364, 2001.

Hassan–Walker et al., "CD8+ Cytotoxic Lymphocyte Responses Against Cytomegalovirus After Liver Transplantation: Correlation Wtih Time From Transplant To Recipient of Tacrolimus," *J. Infect. Dis.* 183:835–843, 2001.

Anonymous, Beckman Coulter™ Press Release (2004) "Study suggests Utility of Beckman Coulter iTAg™ MCH tetramer technology for predicting development of CMV disease in stem cell transplant patients".

* cited by examiner though the binding affinity of the pp65495-503 epitope to HLA A*0201 is only moderately strong.

CTL EPITOPE ANALOGS

CROSS-REFERENCE TO RELATED APPLICATIONS

This application is a divisional application of U.S. Ser. No. 09/692,325 tiled Oct. 20, 2003, now U.S. Pat. No. 6,632,435, which claims the benefit of U.S. provisional application Ser. No. 60/160,633 filed Oct. 20, 1999 and U.S. provisional application Ser. No. 60/187,871 filed Mar. 8, 2000.

STATEMENT REGARDING FEDERALLY SPONSORED RESEARCH

This invention was made with government support in the form of Grant Nos. CA30206 and CA77544 from the National Cancer Institute. The United States Government may have certain rights to the invention.

BACKGROUND OF THE INVENTION

1. Technical Field

This invention relates to peptide ligands from viruses, e.g., human cytomegalovirus (HCMV) with improved immunogenicity wide recognition among HLA subtypes and methods for their production. These peptides are able to activate cytotoxic T lymphocytes at extremely low concentrations and therefore are suitable for use as vaccines.

2. Description of the Background Art

The HCMV genome is relatively large and has the capacity to encode more than 200 proteins. HCMV is composed of a nuclear complex of double-stranded DNA surrounded by capsid proteins having structural or enzymatic functions, and an external glycopeptide and glycolipid-containing membrane envelope. HCMV is a member of the Herpes virus family and has been associated with a number of clinical syndromes.

HCMV infection is relatively common and is usually self-limiting in the healthy, immunocompetent child or adult. However, approximately 10% of all newborn infants carry HCMV; the virus can cause severe congenital disease in the fetus or infant. For example, HCMV is a common cause of mental retardation in children who acquire the infection in utero from mothers carrying an active infection. Some of these newborn infants suffer congenital birth defects; others carry cytomegalovirus for some time before they show symptoms of the disease.

Other syndromes have been noted in persons carrying a persistent and apparently asymptomatic HCMV infection, for example, restenosis. HCMV is also associated with morbidity and mortality in immuno-compromised patients, such as patients suffering from acquired immunodeficiency syndrome (AIDS). AIDS patients infected with HCMV often suffer impairment of some of their vital organs, including the salivary glands, brain, kidney, liver and lungs as a result of the effects of HCMV disease. Furthermore, HCMV is associated with a wide spectrum of classical syndromes including mononucleosis and interstitial pneumonia. HCMV also has oncogenic potential and possible association with certain types of malignancies, including Kaposi's sarcoma.

Because human cytomegalovirus is relatively common, yet is associated with some extremely serious health conditions, considerable effort has been made to study the biology of the virus with the aims of improving diagnosis and developing preventive and therapeutic strategies.

Viral infection of a host stimulates the processing of viral proteins through the Class I pathway, resulting in antigenic peptides which are presented by antigen presenting cells in the context of cell-surface MHC Class I. A $CD8^+$ CTL response is an important part of a mammalian host's response to certain acute viral infections. Differentiation of $CD8^+$ T cells into mature CTL generally leads to clearance or control of the viral infection. The observations that HCMV infection is wide-spread and persistent and can become reactivated and clinically important in the immunosuppressed patient, suggest that virus-specific T cells, including HCMV-specific CTL, play an important role in both the control of persistent infection and recovery from HCMV disease. In a $CD8^+$ CTL response, a processed form of a viral protein (a minimal cytotoxic epitope) is recognized by $CD8^+$ CTL in combination with MHC Class I molecules. A minimal cytotoxic epitope of 8–12 amino acids can prime an antigen presenting cell to be lysed by $CD8^+$ CTL, as long as the correct MHC molecule is expressed on its surface.

Certain viral structural proteins which exist in large quantity in the viral particle, such as pp65 in HCMV, are chaperoned into infected host cells early in infection. Structural virion proteins are immuno-dominant target antigens important in the production of HCMV-specific CTL responses. The pp65 protein has been identified as a target antigen which is present in the peripheral blood of most asymptomatic HCMV seropositive individuals. McLaughlin-Taylor et al., *J. Med. Virol.* 43:103–110 (1994). The $pp65_{495-503}$ CTL epitope (SEQ ID NO: 1; NLVPMVATV) from HCMV is universally recognized among HCMV-seropositive individuals who express HLA A*0201. Moreover, CTL against $pp65_{495-503}$ recognize and lyse HCMV infected cells in vitro within an hour of infection. Thus, these CTL which recognize $pp65_{495-503}$ may be important for limiting HCMV reactivation and progression of HCMV disease. The ability to induce a cellular immune response to pp65 therefore is extremely important in protecting both immuno-compromised and normal individuals from HCMV disease. However, the binding affinity of the $pp65_{495-503}$ epitope to HLA A*0201 is only moderately strong.

One method of eliciting virus-specific CTL is to immunize with a vaccine peptide representing a minimal cytotoxic epitope defined for a viral antigen in the context of a particular MHC restriction element. Such a vaccine boosts the CTL memory response to the virus in individuals carrying that MHC restriction element. Vaccine developers have become increasingly interested in immunizing with minimal cytotoxic epitopes rather than virus proteins because they can bind to MHC Class I molecules in the host through direct binding of the cell surface molecules without internalization or processing.

Individual MHC Class I molecules preferentially bind peptides of a given motif. The amino acid sequence of specific positions of the motif known as "anchor positions" are invariant. Falk et al., *Nature* 351:290–296 (1991). Amino acid positions other than the anchor position also contribute to a lesser degree to the specificity of peptide binding to MHC Class I molecules. Additionally, residues at positions within the CTL epitope which do not interact with MHC may interact with T cells. Some amino acid residues of the epitope contact the T cell receptor of the responding T cell, some contact the MHC restricting allele expressed on an antigen presenting cell, and some do not strongly contact either. Fremont et al., *Science* 257:919–927 (1992); Madden et al., *Cell* 75:693–708 (1993); Ono et al., *J. Immunol.* 161:5454–5463 (1998). The binding of amino acid residues to MHC or T cell receptor structures is independently governed, so that substitution of T cell receptor binding amino acid residues in some cases will not interfere with the binding to the MHC molecule on the surface of an antigen presenting cell. Sette et al., *Mol. Immunol.* 31:813–822 (1994); Vierboom et al., *J. Immunother.* 21:399–408 (1998); Valmori et al., *J. Immunol.* 161:6956–6962 (1998).

Peptides from the melanoma-specific antigen gp-100 have been altered at the anchor positions for increased binding to HLA A*0201, which resulted in the increased efficiency of stimulation of CTL from melanoma patients. Parkhurst et al., *J. Immunol.* 157:2539–2548 (1996). Similarly, CTL epitopes specific for murine H-2 $K^d$, $K^b$ and $D^b$ were substituted at anchor positions, resulting in enhanced immunogenicity. Vierboom et al., *J. Immunother.* 21:399–408 (1998). On the other hand, directed substitution at anchor positions did not produce ligands that stimulated high-affinity CTL directed toward cancer antigens which were able to cause tumor regression. Clay et al., *J. Immunol.* 162:1749–1755 (1999). Therefore, different approaches need to be considered in defining residue substitutions that might influence the immunogenicity and vaccine properties of the $pp65_{495-503}$ CTL epitope. The complexity of the molecular interactions between the individual molecular components of the immune system complex (TCR, peptide and MHC) has thwarted most attempts at significantly enhancing the binding affinity and immunogenicity of most peptide MHC ligands. Clay et al., *J. Immunol.* 162:1749–1755 (1999); Parkhurst et al., *J. Immunol.* 157:2539–2548 (1996); Leggatt et al., *J. Immunol.* 161:4728–4735 (1998).

In most cases, CTL epitopes are between 8–11 amino acids long as determined by either mass spectrometry or Edman degradation of peptides eluted from MHC molecules. Peptides which bind to MHC molecules after infection with virus are referred to as "naturally processed epitopes." These peptides require no further proteolytic processing to sensitize the transporter for antigen processing (TAP) deficient cell line, T2, for CTL-mediated lysis. Synthetic peptides having the sequence of these minimal length peptides (and certain variants) also can bind to MHC molecules and sensitize targets for lysis by CD8+ CTL. Rammensee et al., *Annu. Rev. Immunol.* 11:213–244 (1993). More importantly, these peptides are capable of eliciting CTL that control or clear viral infections. Del et al., *J. Virol.* 65:3641–3646 (1991); Schulz et al., *Proc. Natl. Acad. Sci. USA* 88:991–993 (1991). An important objective therefore is to develop vaccination strategies that will successfully combat disease utilizing CTL epitopes or their analogs.

SUMMARY OF THE INVENTION

Accordingly, this invention comprises a method of producing a human cytomegalovirus peptide cytotoxic T lymphocyte epitope analog with improved immunogenic potency and retained breadth of recognition of MHC allele subtypes relative to the native human cytomegalovirus peptide cytotoxic T lymphocyte epitope which comprises providing a sequence of a human cytomegalovirus peptide cytotoxic T lymphocyte epitope and a combinatorial peptide library which contains peptide analogs of said viral peptide cytotoxic T lymphocyte epitope; screening said combinatorial peptide library for immunogenicity; analyzing the results of said screening to select one or more peptide analogs which may have improved immunogenicity relative to the native human cytomegalovirus peptide cytotoxic T lymphocyte epitope; assaying said one or more peptide analogs for immunogenicity; analyzing the results of the assay in step (d); selecting one or more highly immunogenic peptide analogs based on the analysis of step (e); assaying said highly immunogenic peptide analogs for broad recognition of MHC allele subtypes; analyzing the results of the assay in step (g); selecting one or more highly immunogenic peptide analogs with retained breadth of recognition of MHC allele subtypes relative to the native human cytomegalovirus peptide cytotoxic T lymphocyte epitope based on the analysis of the earlier steps; and synthesizing the peptides selected in step (i). In another embodiment, the invention provides a method which further comprises, before synthesizing the peptides, creating a library of peptide analogs from the highly immunogenic peptide analogs of step (f) containing substitutions of the native viral peptide cytotoxic T lymphocyte epitope; assaying said library of peptide analogs containing substitutions of the native viral peptide cytotoxic T lymphocyte epitope for both immunogenicity and breadth of recognition of MHC allele subtypes; and analyzing the results of the assays in step (B).

In further embodiments, the invention provides cytotoxic T lymphocyte epitope analogs produced according to the methods described above, for example, SEQ ID NOS: 38, 52 and 64. In further embodiments, the invention provides vaccines comprising such peptides.

BRIEF DESCRIPTION OF THE DRAWINGS

FIGS. 3A through 3I present data from peptide positions 1 through 9, respectively. The residue present in the native sequence at each position is represented by a hatched bar, while the remaining amino acids are represented by solid bars.

DETAILED DESCRIPTION OF THE PREFERRED EMBODIMENTS

Figure 1:
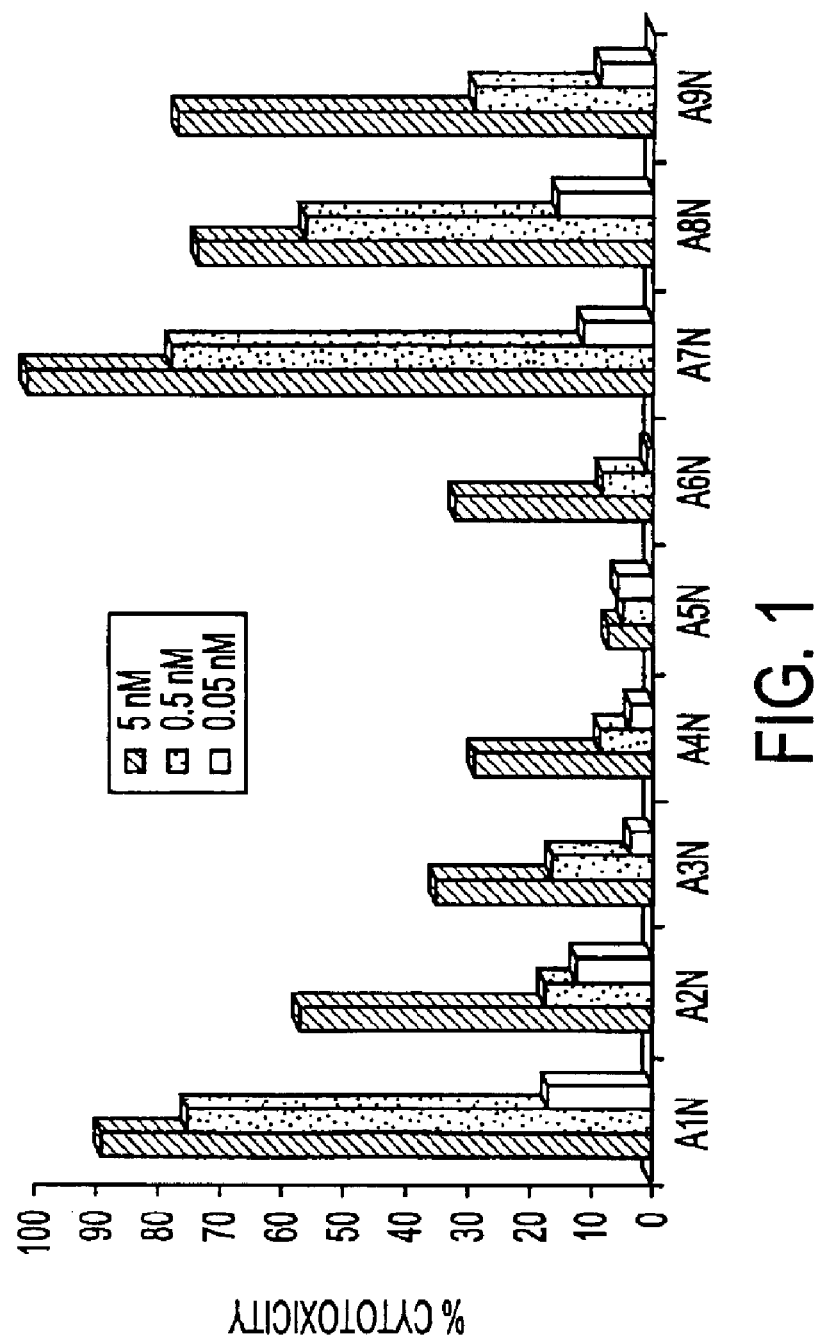
FIG. 1 is a bar graph presenting cytotoxicity data for antigen presenting cells loaded with the indicated carboxyl terminal amidated peptides.

Multiple TCR sequences are used to recognize the native viral sequences such as $pp65_{495-503}$ by different individuals. Solache et al., *J. Immunol.* 163:5512–5518 (1999); Weekes et al., *J. Virol.* 73:2099–2108 (1999). It is of great interest to understand what common elements of native sequences allow them to be recognized by individuals with diverse TCR repertoires, as a means to design universally recognizable CTL epitope analogs of higher immunogenicity in the context of fighting a viral infection such as HCMV. Whether vaccine peptides can maintain an equivalent breadth of recognition as the native peptide sequence (i.e., $pp65_{495-503}$) is an important criterion for their value to the public health. If vaccine peptides are only recognized by a small subset of individuals, then their usefulness is limited. The immunodominance of viral peptides like $pp65_{495-503}$ provides a circumstance in which careful selection of residues can produce a peptide which provides both maximum immunogenic effect and very wide recognition.

Preferably, antiviral vaccines should suppress both primary infection and reactivation of persistent or latent virus. A robust humoral response to major surface glycoproteins may be adequate to prevent new infection, but usually will not prevent reactivation of latent virus, which is spread through cell-cell contact. A cellular immune response capable of lysing infected cells which destroys the intracellular store of virus, therefore, is a goal of any vaccine strategy, and particularly for HCMV.

Once HCMV infection is established, HCMV persists throughout life. Healthy HCMV-seropositive adults maintain a large fraction of circulating CTL with specificity against the virus but the virus is not cleared. Interference with antigen presentation may limit the effectiveness of ongoing adaptive immunity. Nonetheless, viremia is seldom found in asymptomatic seropositive donors. In contrast, individuals who are immunosuppressed after bone marrow transplantation or virus infection (e.g., HIV) often have active HCMV viremia. Augmentation of viral immunity by eliciting greater numbers of CTL, more potent CTL or both would limit viremia and prevent disease to a large extent. Because pp65 is the main target of cellular immunity in asymptomatic adults, a vaccine against HCMV will likely need to enhance immunity against pp65 to be successful. Enhancing the immunogenicity of CTL epitopes from pp65 which are recognized by the adaptive immune system is a potent strategy to overcome HCMV viremia and disease.

Peptide ligands such as $pp65_{495-503}$ can activate CTL for target lysis with a sensitivity in the nanomolar range. Diamond et al., *Blood* 90:1751–1767 (1997). Some other CTL epitopes derived from pp65 or other viral proteins can sensitize lysis of antigen presenting cells in the picomolar range, however these more potent viral proteins often are not recognized as frequently by large human populations. Busch et al., *J. Immunol.* 160:4441–4448 (1998); Gallimore et al., *J. Exp. Med.* 187:1647–1657 (1998); Vierboom et al., *J. Immunother.* 21:399–408 (1998). It would be advantageous to develop a CTL epitope which retains near universal recognition and yet has enhanced immunogenicity. This would improve the effectiveness of anti-viral peptide vaccines and reduce the amount of peptide needed to obtain a clinically relevant immune response. To be of greatest clinical value from a public health perspective, the vaccine peptide analog would preferably retain the ability to be recognized and to stimulate CTL expressing most or all subtypes of the appropriate HLA group, for example HLA A*0201. Therefore, the terms "immunogenic," "immunogenicity" or "immunogenic potency" refer to the ability to stimulate cytotoxic T lymphocytes at a relatively low concentration. The term "retained breadth of recognition of MHC allele subtypes" refers to the ability of the epitope to be recognized by a range of cytotoxic T lymphocytes possessing different MHC allele subtypes.

In vitro stimulation was employed to establish the extent of recognition of the $pp65_{495-503}$ epitope among seropositive HLA A*0201 individuals and further confirm that $pp65_{495-503}$ epitopes can stimulate CTL that will recognize HCMV-infected fibroblasts. A survey of 10 individuals confirmed its wide recognition. Since there is little natural variation of the $pp65_{495-503}$ sequence at any of the nine positions, there is no easy way to predict the tolerance of amino acid sequence modification of the epitope.

To predict the immunogenic potency effect of extensive amino acid residue changes in a CTL peptide epitope, it is useful to begin by identifying which amino acid residues may be changed without reducing immunogenicity. An alanine substitution study, for example, allows one to perform such a study quickly and easily. To perform this type of study, a series of peptides may be synthesized which contain an alanine substitution at each different position along the sequence to be tested. For example, Table I shows the structure of alanine-substituted peptides for use in an alanine-substitution study of the native residues in each position of $pp65_{495-503}$ (SEQ ID NO:1; NLVPMVATV). Each alanine-substituted peptide may be synthesized with either a free acid carboxyl terminus or an amide terminus or both may be synthesized. The peptides then may be used to sensitive antigen presenting cells, which can be screened for lysis by the T cell clone of interest. Of course, substitution may be made with alternative amino acids if convenient. Those of skill in the art of peptide design and combinatorial chemistry are well aware of different methods to investigate the effects of residue substitutions, and these are contemplated for use here.

It is useful to screen different peptides for cellular immunogenicity or the ability to lyse antigen presenting cells which present the viral epitope. An efficient way to accomplish this is to screen a peptide library. The combinatorial chemistry approach is preferred, however those of skill in the art are aware of many methods to obtain and test a number of peptides. A more robust approach than single amino acid substitution makes use of combinatorial chemistry to produce simultaneous large arrays of multiply-substituted peptides. The library approach for studying T cell epitopes can be combined with information gained from MHC anchor studies, or alanine substitution. A convenient method to screen a large number of peptides to obtain information allowing a correlation of immunogenicity and changes in peptide sequence at specific locations is through a positional scanning synthetic combinatorial library.

An important attribute of a PS-SCL sub-library to simultaneously scan all possible residue combinations at all positions of an epitope, which may predict a better choice than a directed amino acid substitution at a single position. Recent studies utilizing the positional scanning format have identified high potency ligands which exceed the binding affinity of the natural ligand. The focus of these previous reports has been either to discover new epitopes, or enhance existing epitope immunogenicity specific to individual inbred mouse strains, or human T cell clone. Gundlach et al., *J. Immunol.* 156:3645–3651 (1996); Hemmer et al., *J. Immunol.* 160:3631–3636 (1998); Wilson et al., *J. Immunol.* 163:6424–6434 (1999). Restricted versus broad recognition of the analog epitopes has not been the main concern of previous studies. In contrast, this invention provides a method of enhancing immunogenicity of a CTL epitope simultaneously preserving the desirable property of universal recognition. Both are necessary properties of a vaccine for broad clinical use.

Positional scanning synthetic combinatorial libraries (PS-SCL) are libraries composed of peptides of uniform length having specific defined positional mutations systematically arranged. A typical PS-SCL comprises a positional sub-library for each position along the length of the peptide. For example, a nonamer PS-SCL comprises nine independent positional libraries, and is represented as $O_1XXXXXXXX$, $XO_2XXXXXXX$, $XXO_3XXXXXX$, $XXXO_4XXXXX$, $XXXXO_5XXXX$, $XXXXXO_6XXX$, $XXXXXXO_7$, XX, $XXXXXXXO_8X$, $XXXXXXXXO_9$ in which $O_1$–$O_9$ each represent a position occupied by a defined amino acid, and X represents positions occupied by any amino acid. An octomer PS-SCL comprises eight positional libraries. Each positional library in the PS-SCL comprises 20 sublibraries in which the "O" position is occupied by a different defined amino acid. The screening of a PS-SCL can provide information about the most important residues at each position of the CTL epitope for strong recognition by a T cell clone.

The length of the epitope specific for a T cell clone is a starting point in selecting an appropriate peptide screening library. For example, the CTL epitope for T cell clone 3-3F4 ($pp65_{495-503}$; SEQ ID NO:1) is a nonamer, therefore a nonamer peptide PS-SCL was selected. Generally, library sub-mixtures for screening are used at a low enough concentration, for example 50–100 μg/mL, such that individual peptides in the sub-mixture are present in vanishingly small amounts (~$5.5\times10^{-15}$ M). Greater or lower concentrations of library peptides may be used as is convenient, depending on the parameters of the screening assay used, however about 10 μg/mL to about 1 mg/mL is preferred and about 50 μg/mL to about 100 μg/mL is most preferred. Even though each individual peptide in the mixture is present in very low concentration, cytotoxic activity against sensitized antigen presenting cells is measurable. Measurable cytotoxic activity indicates that one or more individual peptide analogs in the mixture nevertheless can trigger T cell responses.

The peptide library is conveniently screened by preparing antigen presenting cells expressing the peptides on their surfaces. These antigen presenting cells can then be loaded with $^{51}Cr$ and assayed for lysis by T cells derived from asymptomatic virus seropositive blood donors who have mounted a cellular immune response to the virus. The sub-mixtures within the library may be screened to determine which groups of peptides result in the greatest cytotoxicity of antigen presenting cells. Once the group or groups of most active peptides are determined, individual peptides advantageously may be synthesized to confirm the results obtained from the screen.

Preparatory experiments with the T cell clones preferably may be carried out to establish the minimal concentration of native peptide ligand which causes sufficient lysis of the HLA-matched antigen presenting cells. A T cell clone that recognizes the peptide bound to lymphocytic cell lines (LCL) advantageously may be used to conduct titration experiments using a limiting number of antigen presenting cells which cause optimal recognition by the peptide at a given concentration.

Peptides may be synthesized by any convenient method known in the art. The peptides are advantageously tested for immunogenicity by assaying lysis of antigen presenting cells presenting the peptides or virus-infected cells. Antigen presenting cells, for example peripheral blood mononuclear cells, dentritic cells or an Epstein-Barr virus immortalized lymphocyte B-cell line, may be obtained by prior art methods such as density gradient centrifugation and the like from any convenient tissue, however peripheral blood is most convenient. Other tissues also may be useful. Culture techniques for maintaining any of these antigen presenting cells are well known in the art and may be adapted according to the cell type chosen.

Antigen presenting cells may be pulsed with peptide by known methods, or any method. Generally, cells may be incubated for about 4 to about 6 hours or for about 2–3 hours with the peptide to be presented. A final peptide concentration of about 100 μM is suitable, however this may vary. About 1 μM to about 500 μM typically can be used. After incubation with the peptide(s), the cells are advantageously exposed to gamma irradiation. About 2,400 rads is sufficient, or any amount to cause the death of the feeder or target cells within about 1–2 days after exposure. Radiation is titrated for individual cell types. For example, typically, 2,500 rads is used for mononuclear cells and up to 5,000 rads is used for lymphoid blast lines or cultured lines, varying upon the sensitivity of the cells to radiation.

Screening assays to determine whether the peptides elicit a cellular immune response directed by virus specific cytotoxic T lymphocytes as known in the prior art are conveniently used. The target cells (antigen presenting cells) described above may be screened for lysis by T cell clones specific for the virus (effector cells). These T cell clones may be prepared from peripheral blood mononuclear cells from healthy virus seropositive blood donors. The cells may be depleted of $CD4^+$, $CD16^+$ and $CD56^+$ cells by any method known in the art, such as by immunomagnetic separation using specific antibodies, and the like. Alternatively, $CD8^+$ cells may be purified by direct immunoseparation, or by any convenient method. These purified or semi-purified CTL may be kept in culture and used as a source of virus specific T cell clones. In vitro stimulation of the T cell cultures with gamma-irradiated fresh, allogeneic peripheral blood mononuclear cells and PHA causes proliferation of the specific T cell clones. A combination of limiting dilution and in vitro stimulation allows the desired clones to be expanded.

For a suitable assay of cytotoxicity, chromium release assays are convenient. Target antigen presenting cells may be loaded with $^{51}$Cr and exposed to the virus-specific CTL. Virus-infected fibroblasts, T2 cells, or any convenient cell may be used as a target, as well as antigen presenting cells loaded with CTL epitope peptides or analogs. After labeling with $^{51}$Cr, the target and effector cells are mixed together with culture and incubated for several hours, for example about 2 to about 16 hours, or about 2 to about 8 hours, or most preferably for about 4 hours. After the incubation, the amount of chromium released from the cells is measured. Generally, it is greatly preferred to perform control incubations to test spontaneous release in the absence of effector cells and maximal total release as controls with each assay performed.

When the candidate vaccine peptides or library peptides have been screened, peptides or peptide groups which have resulted in significant immunogenicity may be individually screened in the same manner to confirm activity. Additional assays may be performed with individual peptides if desired. For the specific peptides exemplified here, an alanine substitution study was performed using the peptides of Table I to determine which amino acids could be changed without losing the recognition needed for cell recognition and cytolysis or which amino acid residues were more flexible in their binding.

In the alanine substitution study, the amidated forms showed prominent recognition differences from their free acid-counterparts, especially at the termini of the epitope. Only slight differences were observed in recognition between the native sequence and analogs with alanine substitution at positions 1, 8, and 9. The data suggested those positions to be tolerant of amino acid substitutions and that the amidated carboxyl terminus uniformly enhanced recognition and sensitivity compared to the free acid forms of the analogs. The results of this study were compared to the results of a comprehensive screen of peptides using a positional scanning synthetic combinatorial library.

The screening of the positional libraries pointed to several CTL peptide epitope analogs which resulted in greater cytotoxicity than the native peptide by chromium release assay. The results for positions 1, 3, 7, and 8 were particularly interesting. The favored defined amino acid sub-library for each of those positions was non-intuitive, based on published motif information; despite showing minimal change in recognition, alanine substitution at positions 1, 3, 8 and 9 was not predictive whether an alanine defined amino acid library from the PS-SCL would be well recognized. Since the sub-libraries are composed of diverse sequences whose only similarity is the single fixed amino acid at one position, linking superior recognition of a positional library to superior recognition of a single peptide sequence in the mixture cannot be made directly. One consistent property of the alanine and PS-SCL screens was the advantage of C-terminal amidation to obtain high level recognition of analogs.

Sequences corresponding to the best recognized defined amino acid library at each of nine positions were selected, and 16 peptides were synthesized as both amidated and free acid forms. Choices of amino acids for positions 1 and 2 were difficult to select, because the differences between sub-libraries was minimal. Since the native peptide is extremely hydrophobic, a decision to avoid phenylalanine in positions 1 and 2 in favor of tyrosine and leucine, respectively. Only two of the 16 predicted peptides were significantly more immunogenic than the native sequence. In 3 of 4 instances in which two amino acids were evaluated at one position, only one provided any benefit to immunogenicity, and in some cases, the alternative proved to be deleterious for recognition or equally tolerated. Significantly, the free acid forms of all 16 peptides proved to be non-immunogenic utilizing either T2 cells or Epstein-Barr virus transformed B cells. In contrast, there was no difference in immunogenicity between the amidated and free acid forms of the native epitope sequence.

Peptides 44N and 46N (YLLPMVVSV-NH$_2$ and YLLPMVTSV-NH$_2$; SEQ ID NOS:2 and 3; see Table II) were assayed individually and found to have greater cytotoxicity, but to have lost the property of wide recognition by different subtypes of HLA A*0201. No T cell clone other than 3-3F4 recognized peptides 44N and 46N, even when antigen presenting cells were sensitized at 5 nM, a saturating concentration for the native sequence. Since the analogs were not cross-reactive with T cell clones specific for the native sequence, the peptides were evaluated by in vitro stimulation to determine whether any distinct memory T cell clone specific for peptides 44 and 46 could be stimulated from peripheral blood. Although peripheral blood from four individuals who responded to the native epitope sequence were stimulated with peptides 44 and 46, only T cells from the individual from whom the PS-SCL screen clone was derived showed any positive response. These results suggest that peptide T cell receptor contacts were altered by insertion of new residues at positions 1, 3, 7, and 8 and it is likely that peptides 44 and 46 are recognized by only a small number of TCR sequences.

To regain the wide recognition of the native sequence, the peptides were modified by substituting back one or more of the native residues as shown in Table IV. These peptides were screened for lysis by several different T cell clones and were found to have regained a measure of the wide recognition enjoyed by the native sequence while retaining the potency of the first peptide analogs. See Table V.

The data showed that restricting the modifications of the native CTL epitope sequence enabled the design of a more universally recognized peptide than the peptides of SEQ ID NOS:2 and 3. One of the peptides demonstrated which is still of greater immunogenicity than the native peptide sequence. The success of these recognition studies in a small cohort of individuals with diverse haplotypes demonstrates the feasibility of these methods in creating improved vaccine peptides which possess both wide recognition and high potency.

Several peptides derived from substitutions of the naturally processed epitope are more immunogenic than the native peptide sequence. The basis for the increase may be related to a change of affinity to either MHC Class I or the TCR. Changes to MHC Class I binding of CTL epitopes can be measured independently from changes in TCR binding affinity using the T2 assembly assay, which measures the relative strength of peptide binding to HLA A*0201. Nijman et al., *Eur. J. Immunol.* 23:1215–1219 (1993); Sette et al., *J.*

*Immunol.* 153:5586–5592 (1994); Zeh et al., *Hum. Immunol.* 39:79–86 (1994). A selection of peptides in both amidated and free acid forms were subjected to the T2 assembly assay.

Peptide binding to MHC Class I measured via the T2-assembly assay only partially correlated with the increased killing activity of key analogs. The forms of peptides 44 and 46 demonstrated substantial binding differences. The contrast between acid and amide forms in binding to HLA A*0201 is not as pronounced for the three more universally recognized analogs (118, 115, and 193). Heightened recognition of the antigen analogs, therefore, is not based solely upon increased affinity to MHC Class I. More likely, the PS-SCL library screening selected peptides having alterations of TCR contact residues that contribute to heightened affinity.

Previous studies have not addressed the concept of improving immunogenicity of epitopes while maintaining broad recognition. Studies which optimize anchor residues of CTL epitopes do not alter T cell contacts since anchor positions mainly bind to MHC Class I. Approaches which have focused strictly on anchor residues, therefore, without regard to other peptide contacts with TCR or MHC have not resulted in dramatic increases in immunogenicity. The degree of flexibility of substitutions at position 1, which tolerated tyrosine in place of asparagine, was not predicted by published motifs, and highlights the strength of the library approach.

An approach to distinguishing how particular substitutions of TCR contact residues contribute to the heightened immunogenicity of analog peptides of $pp65_{495-503}$ is to utilize a soluble HLA reagent that only recognizes TCR after binding specific peptide using an HLA-Ig dimer. See the methods of Carruth et al., *AIDS Res. Hum. Retroviruses* 15:1021–1034, (1999) and Greten et al., *Proc. Natl. Acad. Sci. USA* 95:7568–7573 (1998). The dimer reagent is a chimera of the HLA Class I $\alpha 1$ and $\alpha 2$ domains attached to the Fab portions of Ig molecules. It specifically labels T cells (from T cell clones or from diverse PBL populations) in combination with specific peptide epitopes from either human or murine sources. Bieganowska et al., *J. Immunol.* 162:1765–1771 (1999); Lebowitz et al., *Cell. Immunol.* 192:175–184 (1999).

Peptide analogs were evaluated using a T cell clone with recognition of $pp65_{495-503}$ equivalent to 3-3F4, but expressing a unique TCR. Three analogs showed 10–30 fold greater immunogenicity than the native sequence (Tables IV and V). The data suggested that a combination of two peptides (118N and 193N) would be more immunogenic and broadly recognized than the native sequence. The failure of all three peptides to be recognized as universally as the native epitope sequence by cross-reactive T cell clone was not unexpected.

To examine whether a separate repertoire exists that recognizes analogs in different individuals, the recognition of the three epitopes that were cross-reactive to T cell clone VB57 were examined by in vitro stimulation, an approach that proved effective for evaluating the native sequence epitope and 44 and 46. The results confirmed that of the three peptides, 118N and 193N were most broadly recognized, and 115N had more limited recognition. Furthermore, all three analogs expanded peripheral blood CTL that not only recognized peptide coated targets, but were able to independently lyse HCMV-infected fibroblasts. In summary, the IVS results are consistent with broad-based recognition Qf two out of three of the analogs. Analogs 118N and 115N have properties that qualify them as vaccines because they are more immunogenic than the native epitope, but are likely recognized by as extensive a population as the native epitope.

Peptides according to the invention may be formulated as vaccines according to any suitable method. Naked peptides may be formulated in a suitable adjuvant or any other pharmaceutically acceptable carrier. Cellular vaccines may be prepared by any known method. HCMV peptides according to the invention may be administered alone, or together with a helper peptide such as the polyclonal helper T lymphocyte peptide, PADRE. The two peptides may be administered together or separately, but it is preferable to administer them in close time proximity.

Alternative vaccines include fusions of the helper CD4 peptide epitope with the CTL epitope. The peptides may be fused in either order and may contain a linker sequence between them if desired. Examples of helper CD4 epitopes are the synthetic sequence PADRE (J. Alexander et al., *Immunity* 1:751–761 (1994)) and tetanus-specific peptides. In some cases, these fusion peptides may not require additional covalent lipid modification or adjuvant when administered by the subcutaneous, intranasal, intraperitoneal or intravenous routes. Alternatively, single stranded DNA containing CpG motifs may be co-administered to provide increased activity of the fusion peptide when simultaneously provided at limiting concentration.

A preferred alternative is to join the antigenic peptide to PADRE such that the two sequences form a single peptide chain. PADRE may be positioned at the N- or C-terminus of the antigenic HCMV peptide, and a linker sequence may be positioned between the two sequences or in front of the N-terminal sequence, if desired.

Peptides of the invention may be lipidated or may lack lipids. Unlipidated peptides, whether incorporating a helper peptide sequence or not, are contemplated by the invention, as are monolipidated, dilipidated or trilipidated peptide vaccines. Suitable lipids which may be linked to the peptide sequence include, but are not limited to palmitic acid, stearic acid, myristic acid, lauric acid, capric acid, decanoic acid and the like. Lipids may be attached to the peptides at any location and by any convenient method known in the art.

Adjuvants may form part of the vaccine formulation. Adjuvants such as complete or incomplete Freund's adjuvant, aluminum hydroxide or the like are contemplated, however a preferred adjuvant, particularly for use in humans, is a DNA adjuvant. Single-stranded DNA adjuvants comprising specific sequences including Cytosine-phosphate-Guanosine (CpG) are known in the art and are contemplated for use with this invention. DNA adjuvants lacking these CpG sequences also are useful with the invention. An exemplary DNA adjuvant may comprise a 20 mer of nucleotides with 2 CpG motifs, or any DNA oligomer, generally about 20 to about 25 nucleotides long. Increased stability of the sequence may be obtained by substituting phosphate groups in the nucleotide backbone with thio groups to create a phosphoro-thioate backbone rather than a phosphoro-diester backbone.

The following non-limiting examples are included to illustrate the invention.

EXAMPLES

Example 1

Peptide Synthesis and Characterization

The alanine-scan acid termini peptides (Table I) were synthesized on a pioneer™ Peptide Synthesizer with MPS Accessory (Perseptive Biosystems™, Foster City, Calif.) at 0.05 mmol scale using Fmoc-L-Val PEG-PS resin and standard L-Fmoc amino acids with HATU/DIPEA activators. The peptide 44/46 amidated sublibrary (Table IV) was synthesized using standard Fmoc protocols, using a Synergy™(Perseptive Biosytems™ 432A, Foster City, Calif.) at 0.025 mmole scale. Amidated peptides were synthesized using the Fmoc protected Val-Rink Amide-MBHA resin (AnaSpec™ Inc., San Jose, Calif.). The peptide 44/46 free acid sub-library (Table IV) also was synthesized as described above using Fmoc Val Wang™ Resin (AnaSpec™ Inc., San Jose, Calif.). The Fmoc L-amino acids used in all syntheses were purchased from Novabiochem™ (San Diego, Calif.) and Perseptive Biosystems™ (Foster City, Calif.). Fmoc-tyrosine, serine, and threonine had t-butyl side chain protection and asparagine had trityl side chain protection.

All peptides were cleaved from the resin and purified according to prior art methods (39). To verify correct mass of the peptide, Matrix Assisted Laser Desorption Ionization Mass Spectrometry (MALDI) was performed on the Kompact™ Probe (Kratos Analytical™, Manchester, UK). HPLC (Schimadzu™ SCL 10AVP) using a $C_{18}$ column of 4.6×250 mm dimension composed of $5\mu$×300Δ Particles (Vydac Separations™, Hesperia, Calif.) also was performed. Sample purity was assessed at 70–80% based on the area percent of the sample peak in the chromatogram. The native pp65495-503 epitope was purchased from Peninsula Laboratories™ Inc. (San Carlos, Calif.) at a purity of 95% established by HPLC.

Example 2

Preparation of Peptide-Loaded Antigen Presenting Cells and In Vitro Stimulation Peptide loaded antigen presenting cells were prepared as follows. Sixty milliliters of human blood was collected in sodium heparin from healthy donors who were serologically typed as HLA A*0201 and HCMV positive. Donors were first screened for HLA type (COH HLA Typing laboratory or National Marrow Donor program) and were subsequently test for HCMV seropositivity by indirect immunofluorescence (Hemagen Diagnostic™, Columbia, Md.). Peripheral blood mononuclear cells were separated using Ficoll-Paque™ (Amersham Pharmacia™, Uppsala, Sweden), and cells were resuspended in phosphate-buffered saline (PBS) and washed two times.

Sixteen to twenty-four million of the ficoll-separated peripheral blood mononuclear cells were incubated 2–3 hours at 37° C. in a 5% $CO_2$ incubator with 100 $\mu$M HCMV PP65$_{495-503}$ peptide (SEQ ID NO: 1) in a volume of 100 $\mu$l of T cell culture medium (IVSTCM). IVSTCM consists of RPMI-1640 supplemented with 20% heat inactivated HAB serum, 10 IU/ml r-IL2 (Chiron™, Emeryville, Calif.); 25 mM Hepes Buffer Solution, 50 U/ml penicillin, 50 $\mu$g/ml streptomycin, 2 mM L-glutamine and 0.5 mM sodium pyruvate (Gibco™, Rockville, Md.). Human $AB^+$ and HCMV seronegative serum (HAB) for IVS studies was obtained from plasma screened for blood group and HCMV status. Extraction of serum from plasma was performed following standard techniques. Pooled HAB serum was heat inactivated at 56° C. for 30 minutes, tested for its ability to support T cell growth, and stored at −20° C. After the incubation period, the cells, now presenting pp65$_{495-503}$ were resuspended in 2 ml IVSTCM, and γ-irradiated (2,400 rads) using the Isomedic Model 19 Gammator (Nuclear Canada, Parsippany, N.J.).

During the peptide incorporation procedure, an additional aliquot of 10–20 million cells from the same freshly separated peripheral blood mononuclear cells was depleted of $CD4^+$, $CD16^+$ and $CD56^+$ cells as follows. The cells were incubated with purified mouse anti-human CD4, CD16 and CD56 monoclonal antibodies (mAB) (Pharmingen™, San Diego, Calif.) at 10 fold of their saturating concentration, for one hour, with gentle mixing at 4° C. M450 Dynabead™ Dynabead goat anti-mouse IgG (Dynal™, Oslo, Norway) were then added to the mAb labeled PBMC to effect indirect immunomagnetic separation. The resulting population was >80% $CD8^+$ as determined using a FAGSCalbur™ fluorescence activated cell sorter (BD Immunocytomeyry Systems™, Palo Alto, Calif.). These depleted PBMC effectors (200,000 cells/ml) were mixed with an equal amount of antigen presenting cells (5 million cells/ml), and plated in a 24-well plate at 2 ml/well. The CTL effectors were incubated at 37° C., in a 5% $CO_2$ incubator for two weeks. They were fed with 10 IU/ml rIL-2 on days 5 and 10, and fresh medium when necessary.

Example 3

Derivation of HCMV-Specific T cell Clones Using Limiting Dilution from IVS Cultures HCMV specific T cell clones were obtained by limiting dilution from the stimulated CTL generated in Example 2. Frozen or fresh cells from the cultures obtained in Example 2 were plated in 96-well U-bottom plates on day 15 of culture at a concentration of 1 or 3 cells/well together with 150,000 γ-irradiated fresh allogeneic peripheral blood mononuclear cells and 0.5 $\mu$g/ml phytohemagglutinin (Murex™, Dartford, UK) in a final volume of 150 $\mu$l of T cell cloning medium (20). After 14 days, proliferating cells from single wells were transferred into single wells of 24-well plates and restimulated a second time with 1 million/well/ml fresh irradiated allogeneic PBMC and PHA as described above. Starting from day 8 after the second restimulation, actively expanding clones (5 to 30 million cells) were tested in a chromium release assay for the ability to specifically lyse cells.

Example 4

Chromium Release Assay

Chromium release assays were performed according to the methods of (20). Briefly, target cell lines (antigen presenting cells which present pp65$_{495-503}$) were labeled for one hour with 200 μCi/ml $^{51}$Cr (ICN™, Costa Mesa, Calif.). HCMV infected targets were prepared as follows. Five-hundred thousand fibroblasts were pretreated with 800 U/10$^6$ recombinant IFN-γ, (Preprotech™, Rocky Hill, N.J.) to upregulate MHC class I expression and HCMV was added at an m.o.i. of 4. Cells were incubated with virus for two hours at 37° C., in a 5% CO$_2$ incubator. Fresh FBM containing IFN-γ was then added and the cells incubated for an additional 14 hours. Infected fibroblasts were trypsinized, labeled with $^{51}$Cr as described above and used in the assay at an effector-to-target ratio (E/T) of 50 and 10. Epstein-Barr virus transformed B cell lines (EBVLCL) were generated following standard technology using the supernatant of EBV-infected marmoset cells. EBVLCL were grown in medium consisting of RPMI-1640 (Gibco™, Rockville, Md.) supplemented with 10% FBS, 10 mM Hepes Buffer Solution (Irvine Scientific™, Santa Ana, Calif.), penicillin, streptomycin and L-glutamine as described for fibroblast medium. The cells used as targets were prepared by pulsing with 50 μm pp65$_{495-503}$ peptide, and used at an E/T of 25 and 5. For PS-SCL screening and titration of analog peptides, T2 cells, maintained as described in Diamond et al., *Blood* 90:1751–1767 (1997), were pulsed with serial peptide dilutions for use as targets for T cell clone effectors at an E/T of 5.

In the assay, loaded targets and effectors were mixed in culture and incubated for four hours, at which time chromium release was measured. Supernatants were collected on filter frames (Skatron™, Oslo, Norway) and radioactivity determined in a Cobra II gamma counter (Packard™, Meriden, Conn.). For each assay, spontaneous release from the target cells in the absence of effector CTL and maximum possible release after treatment with 2% SDS (Baker Chemicals™, Phillipsburg, N.J.) was determined. Specific cytotoxicity was defined as: 100×[(Re–Rs)/Max–Rs)], where Re=experimental release, and Rs=spontaneous release. Chromium release assays in which lysis without addition of peptide was 20% or greater, or in which spontaneous lysis was 30% or more of the maximal release were considered unacceptable and not reported.

Example 5

Analysis of Individual Substitutions in Alanine Substituted Peptide Ligands.

The alanine-substituted pp65$_{495-503}$ epitope peptides given in Table I were prepared as described in Example 1 using T2 cells as the antigen presenting targets. The nine peptide sequences were synthesized with either an amidated or free acid terminus. A terminal "C" in the peptide name in Table I and in all following tables indicates a carboxyl terminus whereas "N" indicates amide. The substitution of a native amino acid for alanine is shown in bold for each position of the nonamer peptide pp65$_{495-503}$. Peptide A7C corresponds to the native sequence (asterisk). These peptides were used to sensitive antigen presenting cells as described in Example 2 at concentrations of 0.05, 0.5 or 5 nM. The cells presenting these 18 peptides were used to test the T cell clone 3-3F4 by the standard four-hour chromium release assay described in Example 4. Experiments were repeated twice on different days with similar results.

Figure 2:
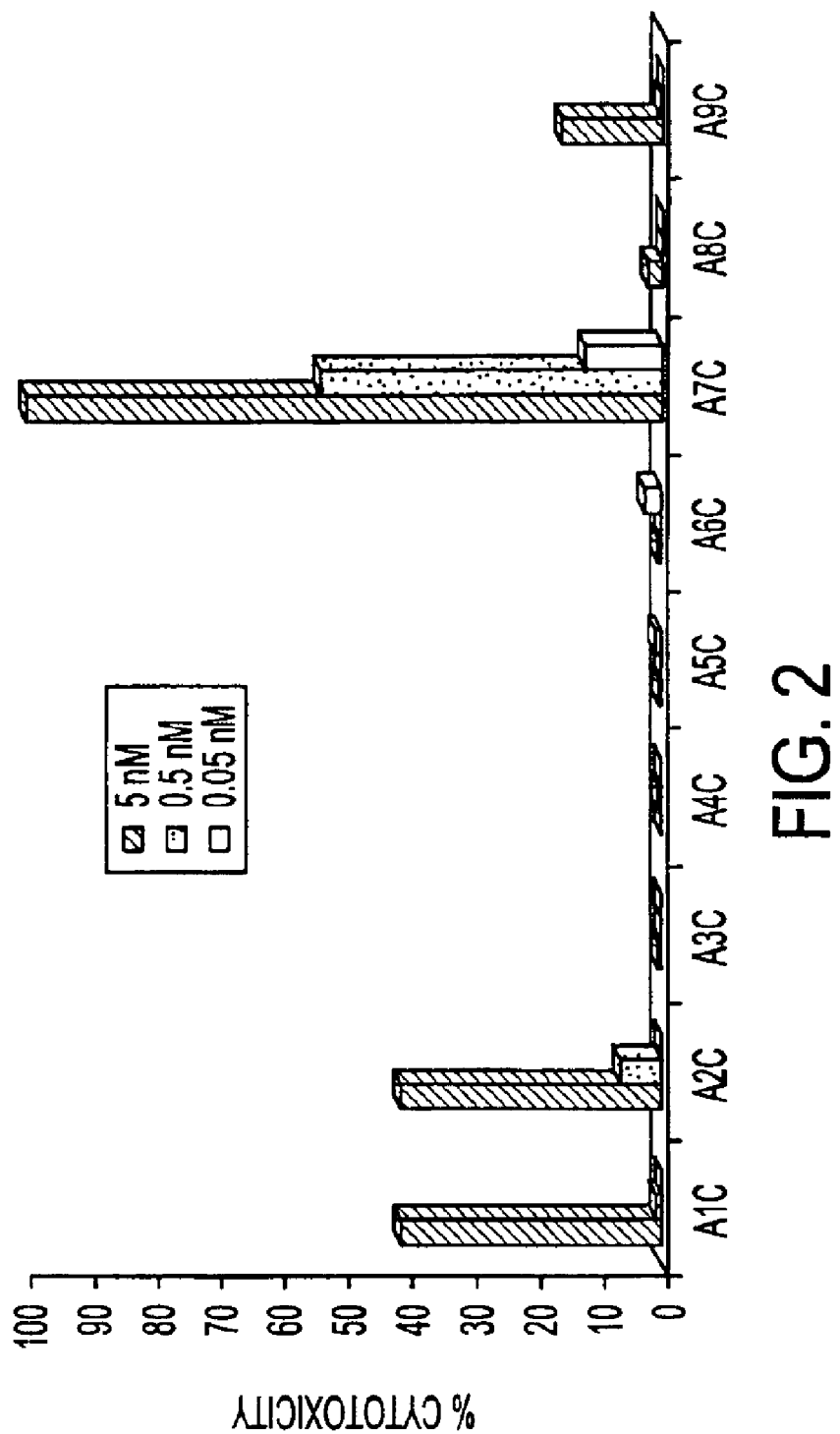
FIG. 2 is a bar graph presenting cytotoxicity data for antigen presenting cells loaded with the indicated carboxyl terminal acid peptides.
Figure 3A:
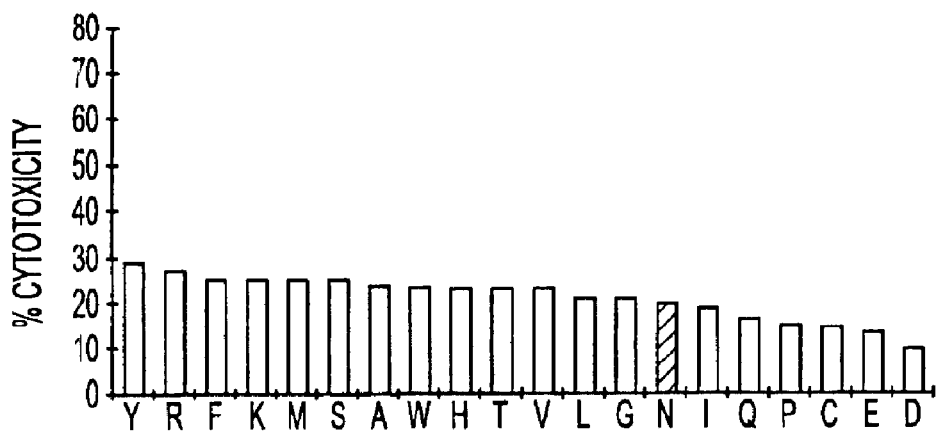
FIGS. 3A to 3I are a series of bar graphs presenting cytotoxicity results from a nomoner PS-SCL screening assay.
Figure 3B:
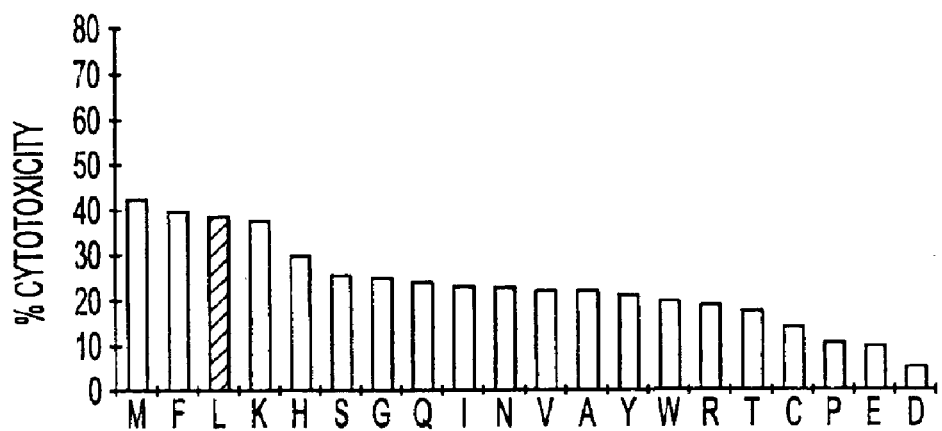
Figure 3C:
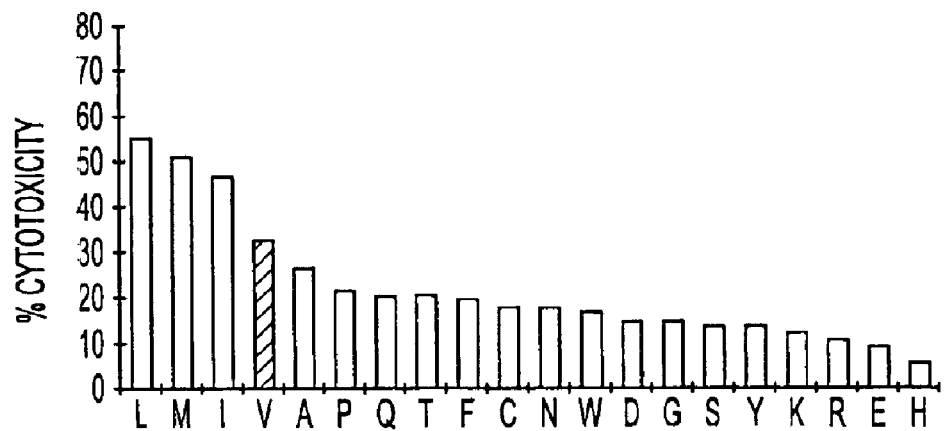
Figure 3D:
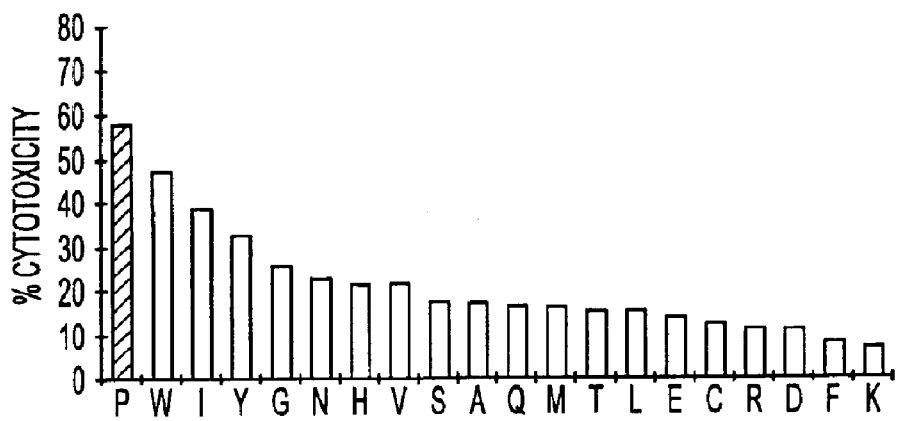
Figure 3E:
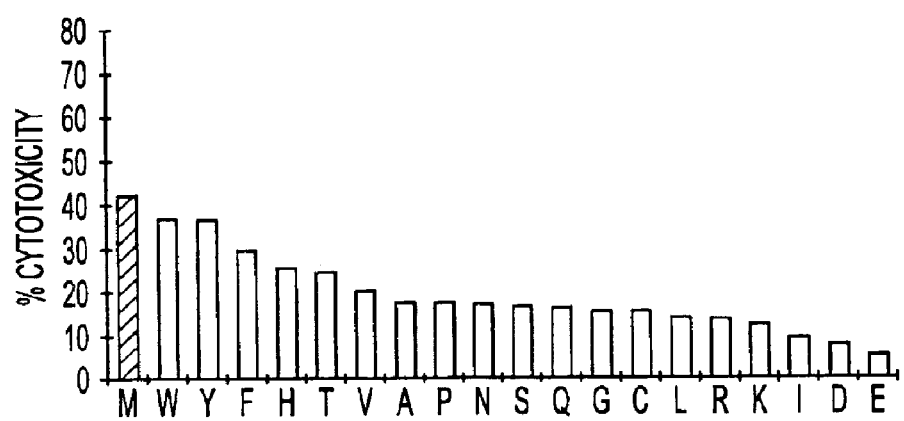
Figure 3F:
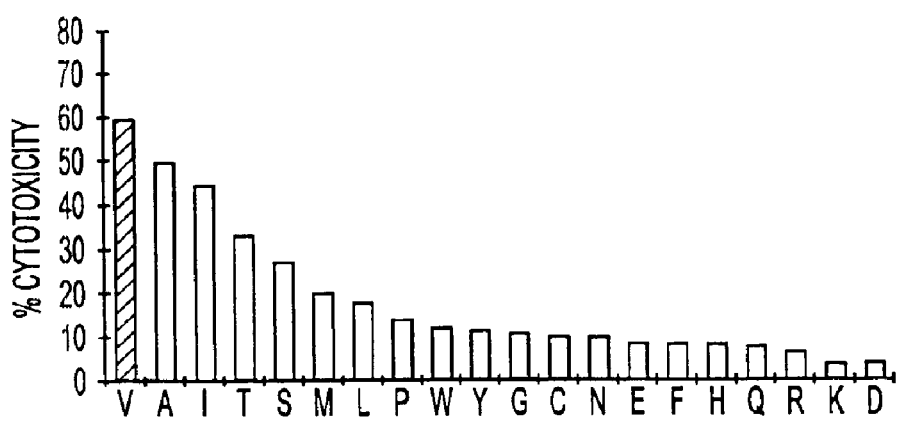
Figure 3G:
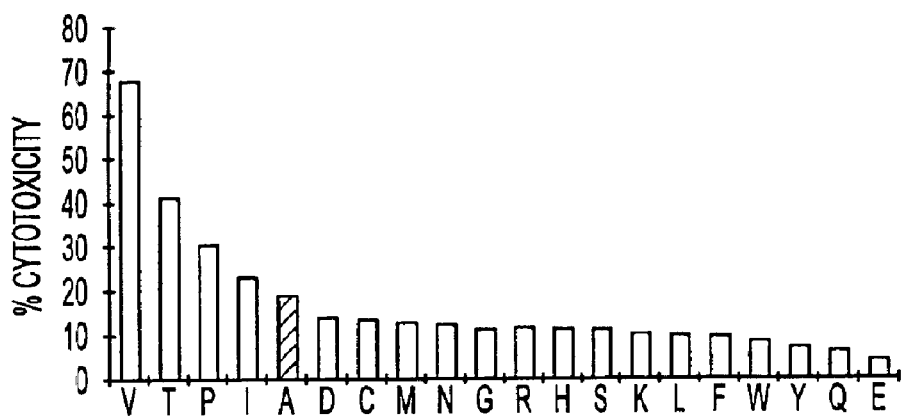
Figure 3H:
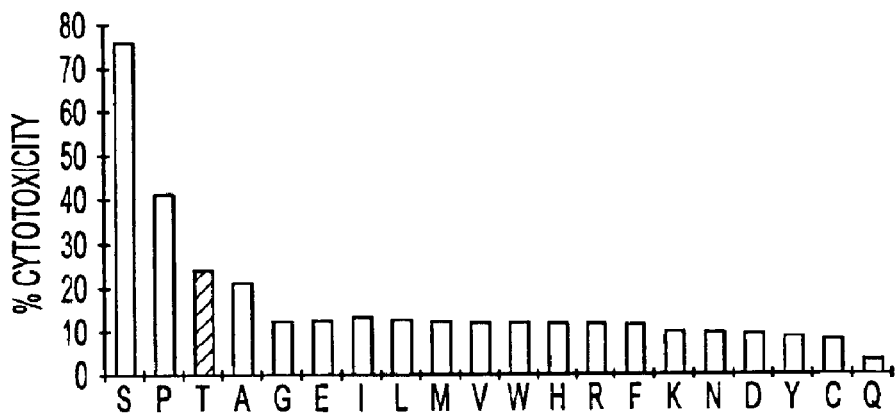
Figure 3I:
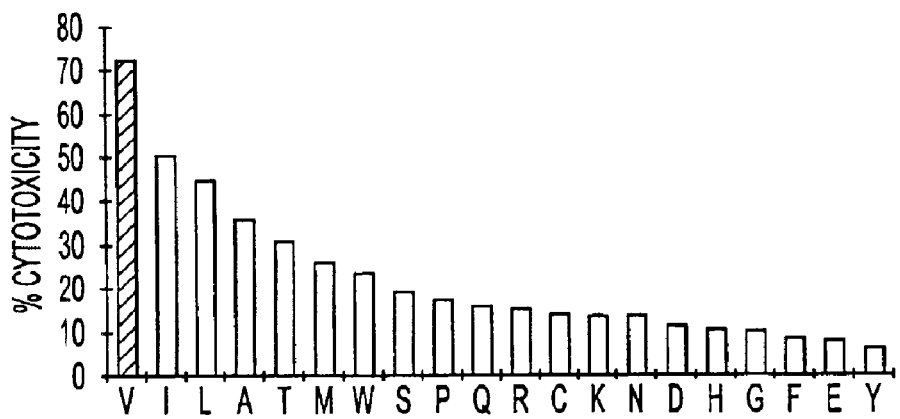

Results are shown in FIGS. 1 and 2.

TABLE I

Alanine Scanning Library of pp65$_{495-503}$ HCMV CTL Epitope.

| Peptide | SEQ ID NO | P1 | P2 | P3 | P4 | P5 | P6 | P7 | P8 | P9 |
|---------|-----------|----|----|----|----|----|----|----|----|----|
| A1C | 4 | A | L | V | P | M | V | A | T | V |
| A2C | 5 | N | A | V | P | M | V | A | T | V |
| A3C | 6 | N | L | A | P | M | V | A | T | V |
| A4C | 7 | N | L | V | A | M | V | A | T | V |
| A5C | 8 | N | L | V | P | A | V | A | T | V |
| A6C | 9 | N | L | V | P | M | A | A | T | V |
| A7C* | 1 | N | L | V | P | M | V | A | T | V |
| A8C | 10 | N | L | V | P | M | V | A | A | V |
| A9C | 11 | N | L | V | P | M | V | A | T | A |
| A1N | 12 | A | L | V | P | M | V | A | T | V |
| A2N | 13 | N | A | V | P | M | V | A | T | V |
| A3N | 14 | N | L | A | P | M | V | A | T | V |
| A4N | 15 | N | L | V | A | M | V | A | T | V |
| A5N | 16 | N | L | V | P | A | V | A | T | V |
| A6N | 17 | N | L | V | P | M | A | A | T | V |
| A7N | 18 | N | L | V | P | M | V | A | T | V |
| A8N | 19 | N | L | V | P | M | V | A | A | V |
| A9N | 20 | N | L | V | P | M | V | A | T | A |

Substitution of alanine for asparagine at position 1, well tolerated by both the amidated and free acid forms of the peptide, based on the slight change (compared to native) in recognition by the T cell clone. In every other position, except positions 8 and 9 for the amidated forms, there was a decline in recognition as a result of alanine substitution of the native residue. The most precipitous decline (compared to native) in recognition occurred for peptides A3N–A6N (amidated analogs), and A3C A6C and A8C (free-acid analogs). In general, the amidated peptide analogs had a greater tolerance for alanine substitutions than the free acid forms. Substitution of the anchor at position 9 by an alanine does not produce a substantial change in cytotoxicity for the amidated form, whereas the equivalent free acid peptide is severely impacted. In summary, positions 1–2 and 8–9 were most tolerant of an alanine substitution as part of carboxyl amidated peptides whereas alanine substitution at positions 3–6 (positions 3–6,8–9 for free acid analogs) caused a precipitous decrease in immunogenicity.

The alanine-substitution study demonstrated plasticity in amino acid residue substitution at several positions of the pp65$_{495-503}$ CTL epitope and suggests that the pp65$_{495-503}$ CTL epitope alanine-analogs have different recognition properties. Addition of an amide moiety to the carboxyl terminus results in a peptide analog with increased tolerance for alanine substitution in every position except position 5.

Example 6

Preparation of Positional Scanning Synthetic Combinatorial Library

Synthetic, C-amide (H-A1-Y9-CONH2) or C-hydroxyl (H-A1-Y9-COOH), L-amino acid combinatorial nonapeptide libraries arranged in a positional scanning format (PCT 97-3) were prepared according to prior art methods using the simultaneous multiple peptide synthesis method. Pinilla et al., *Biotechniques* 13:901–905 (1992). Each library consisted of 180 mixtures in the $OX_8$ format where O represents one each of the 20 natural L-amino acids at a defined position and X represents any of the 20 natural amino acids, with the exception of cysteine, in each of the remaining positions. The first mixture had alanine (A) in position 1 ($A_1X_8$), while mixture number 180 had tyrosine (Y) in position 9 ($X_8Y_9$). Each $OX_8$ mixture therefore consisted of $1.7\times10^{10}$ ($19^8$) different nonamer peptides in approximate equimolar concentration, and the total $X_9$ library consisted of $3.1\times10^{12}$ ($9\times20\times19^8$) different peptides. Assuming an average molecular weight of 1080 for each nonamer and a concentration of 100 µg/ml (93 µM) for nonapeptides in a mixture, the average concentration of individual nonapeptides in a mixture was about $5.5\times10^{-15}$ M.

Example 7

PS-SCL Screen with T Cell Clone 3-3F4

To identify a nonapeptide or nonapeptides having greater immunogenicity than the native peptide, two different nonamer PS-SCL were tested, one containing peptides with an amidated C-terminus, and the other peptides with a free acid C-terminus. The library screening was carried out as follows. Separate aliquots of T2 cells were pulsed with one of 180 mixtures (50 µg/ml) that make up the PS-SCL, and incubated with 3-3F4 cells as described in Example 2.

Two separate screenings were carried out on different days for each test peptide mixture with similar results. Results from preliminary experiments (data not shown) showed that 5000 antigen presenting cells at an E:T ratio of 5 was optimal, therefore, these conditions were used to screen the PS-SCL. The results of the amidated nonapeptide PS-SCL screen are shown in FIGS. 3A–3I. All experimental points were obtained at the same time, and results shown represent the average of two experiments done on different days. The amidated nonapeptide PS-SCL generally gave significantly better results; mixtures at each position resulted in specific recognition and lysis. The variant peptides induced between 0 and 90% specific cytotoxicity in the cells presenting them. Background (without peptide) was 5.0%. The highest specific cytotoxicity results for each position were approximately equivalent to the results obtained with T2 antigen presenting cells pulsed with 1.0 and 10 nM native $pp65_{495-503}$ epitope in a titration that was carried out simultaneously with the library screen (data not shown). In all positions the mixture having the defined amino acid that corresponds to the native peptide showed specific lysis higher than 20%. The $pp65_{495-503}$ epitope sensitized 50% maximal lysis of T2 cells by 3-3F4 at 0.02 nM, yet in many instances lysis exceeds 50%. There are striking levels of recognition stimulated by one or mixtures at each position. The concentration of each peptide in the loading mixture is 95.5 fM, therefore the results suggest that one or more peptide(s) of high potency is responsible for the activity of the mixture.

Mixtures defined with the native amino acids residues at the anchor positions 2 and 9 are among the highest responders at those positions, as expected. For example, the library screen indicates that the valine mixture for P9 is best recognized, which is identical to the native epitope sequence. Interestingly, peptide mixtures with defined amino acids which were ranked slightly lower than valine at P9, were either of neutral charge, or contained aliphatic side chains, such as isoleucine, leucine, or alanine. Although leucine is considered an alternative residue at position 9, its recognition in the screen was substantially less than valine. Mixtures having charged or more polar amino acids were ranked significantly lower, which confirms their non-preference as anchors for HLA A*0201 binding peptides. Although more ambiguous than in the case of P9, the higher ranked mixtures for P2 (M,F,L) are also consistent with preferred residues for the P2 anchor position based on published motifs. This result substantiates the concept of using PS-SCL to modify this CTL epitope, because the screen accurately predicted the sequence of the anchor residues for $pp65_{495-503}$.

For position 1, most mixtures show similar activities, ranging from 15–30% specific lysis, suggesting that a number of amino acids are acceptable at this position. The equivalence of these mixtures suggests that the F pocket of the MHC Class I binding groove can tolerate either an uncharged amino acid containing an aliphatic side chain, or a methionine (75).

Position 3 is occupied by valine in the native sequence. Mixtures defined with the neutral amino acids leucine, methionine and isoleucine showed higher activity than the valine mixture, while the alanine mixture was only slightly less active. The substantial difference in recognition of the three highest ranked mixtures, compared to all others suggests a preference of those residues at position 3. The best recognized mixture for position 4 is proline, which is identical to the native sequence. Mixtures defined with hydrophobic amino acids such as tryptophan, isoleucine, and tyrosine were also active. The mixture choice for position 5 is compatible with the native methionine residue or larger hydrophobic amino acids containing benzene rings (tryosine, tryptophan or phenylalanine). There is not a substantial difference in recognition of the top 3 choices for position 5, nor is the level of lysis as high as the surrounding positions. Interestingly, the methionine at position 5 is negatively affected by any substitution, including alanine, among individually synthesized peptides. It is likely oriented away from the MHC peptide binding pocket, making it available for TCR contact according to molecular modeling simulations (data not shown).

For position 6, the valine mixture is best recognized, and the second and third-ranked choices have fixed amino acids of similar structure. Position 6 likely requires a small neutral-charged amino acid for interaction with either MHC and/or TCR, independent of other substitutions. Between positions 7–9, the highest ranked mixtures are significantly better recognized than lower ranked ones. Position 7 and position 8 provide the most dramatic difference between the highest ranked mixtures, and those that follow. Significantly, mixtures which correspond to the native amino acids are substantially less recognized than the preferred mixtures. For both positions 7 and 8, there is little correlation between the ranking of subsequent mixtures and the structure of the fixed amino acid. The recognition of the alanine and threonine mixtures at P8 are equivalent (FIGS. 3A–3I) which is consistent with results from the alanine-substitution study. The PS-SCL screen showed that the best mixtures had either serine or proline at position 8. Table II presents the amino acid sequences of the peptides predicted by the screen to bind to T cell clones more strongly than the native sequence.

Positions 1, 3, 6 and 9 were substituted with the fixed amino acid corresponding to the top ranked mixture. In some cases, the top two amino acids were selected (as for positions 4, 5, 7 and 8) when the top two ranked mixtures were recognized almost equivalently. The 16 antigen-analogs were pulsed onto antigen presenting cells and evaluated by conducting a chromium release assay with the screening T cell clone, 3-3F4. The modified peptides were made as carboxyl-terminal amides, to be consistent with the structure of the peptides contained in the PS-SCL screening library. Two of the peptides were better recognized than the native epitope sequence by the T cell clone. These peptides (46N and 44N) were both tetra-substituted and were able to induce lysis at concentrations lower than the native epitope. Examination of the common elements of the sequence of peptides 44N and 46N, revealed a serine at position 8. This amino acid resulted in the most potent of all 20 amino acid sub-libraries tested at position 8 (FIGS. 3A–3I). Interestingly, peptides 45 and 47, which share many of the substitutions of peptides 44 and 46, but which contain a proline at position 8, were less active than the native sequence. Thus, the ranking of mixtures in the initial screen conforms to the recognition properties of the individual substitution peptides tested here. A re-screen of the same T cell clone (3-3F4) by a C-terminal free acid library resulted in uniformly low recognition of all sub-libraries, even those having fixed amino acids that correspond to the native sequence (data not shown).

Peptides 44C and 46C were assayed to compare the sensitivity of recognition of the amide versus free acid form of the peptides. Unexpectedly, the absence of the carboxyl terminal amide eliminated recognition of both peptides by T cell clone 3-3F4 and all other T cell clone evaluated (data not shown). The native pp65$_{495-503}$ sequence was synthesized with an amidated carboxyl terminus, and compared to the free acid form by chromium release assay. The amidated peptide was recognized without a significant change of activity compared to the free acid terminated sequence. See Table II. This is consistent with the results of the alanine substitution study which suggested that greater flexibility of substitution is tolerated when the C-terminus is amidated (compare amidated to free acid results, Table II).

TABLE II

Cytotoxicity Results from Potent Nonomer Peptides.

| Peptide Name | SEQ ID NO | P1 | P2 | P3 | P4 | P5 | P6 | P7 | P8 | P9 | Conc. (nM) |
|---|---|---|---|---|---|---|---|---|---|---|---|
| 44N | 2 | Y | L | L | P | M | V | V | S | V | 0.00005 |
| 46N | 3 | Y | L | L | P | M | V | T | S | V | 0.0005 |
| 54N | 21 | Y | L | L | W | M | V | T | S | V | 0.5 |
| 56N | 22 | Y | L | L | W | Y | V | V | S | V | 50 |
| 47N | 23 | Y | L | L | P | M | V | T | P | V | 500 |
| 52N | 24 | Y | L | L | W | M | V | V | S | V | 500 |
| 53N | 25 | Y | L | L | W | M | V | V | P | V | 500 |
| 55N | 26 | Y | L | L | W | M | V | T | P | V | 500 |
| 58N | 27 | Y | L | L | W | Y | V | T | S | V | 500 |
| 45N | 28 | Y | L | L | P | M | V | V | P | V | >500 |
| 48N | 29 | Y | L | L | P | Y | V | V | S | V | >500 |
| 49N | 30 | Y | L | L | P | Y | V | V | P | V | >500 |
| 50N | 31 | Y | L | L | P | Y | V | T | S | V | >500 |
| 51N | 32 | Y | L | L | P | Y | V | T | P | V | >500 |
| 57N | 33 | Y | L | L | W | Y | V | V | P | V | >500 |
| 59N | 34 | Y | L | L | W | Y | V | T | P | V | >500 |
| 44C | 35 | Y | L | L | P | M | V | V | S | V | >500 |
| 46C | 36 | Y | L | L | P | M | V | T | S | V | >500 |
| A7N | 18 | N | L | V | P | M | V | A | T | V | 0.5 |
| A7C | 1 | N | L | V | P | M | V | A | T | V | 0.5 |

Example 8

Cytotoxicity of Nonamer Peptides Predicted from PS-SCL Screen

The native sequence of the pp65$_{495-503}$ CTL epitope is shown at the bottom of Table II. Substitutions predicted by the library screen of T cell clone 3-3F4 are shown on top of the table below each residue position of the CTL epitope. Peptides with carboxyl terminal amidation are named ending in "N," while carboxyl terminal free acid peptides are named ending in "C."

Nonamer peptides with the substitutions as shown at each position were synthesized as described in Example 1. Chromium release assays were performed using peptide sensitized HLA A*0201-restricted EBVLCL as target cells and T cell clone 3-3F4 effectors at E:T=5. Results of these assays are shown in the right-hand column of Table II, in terms of concentration of peptide (nM) in which specific killing was between 15 and 30 percent. Results presented are the average from at least three independent experiments carried out on different days using different batches of T cell clone-3F4. Peptides were tested using 10-fold dilutions, ranging from 500–0.00005 nM.

Example 9

Figure 4:
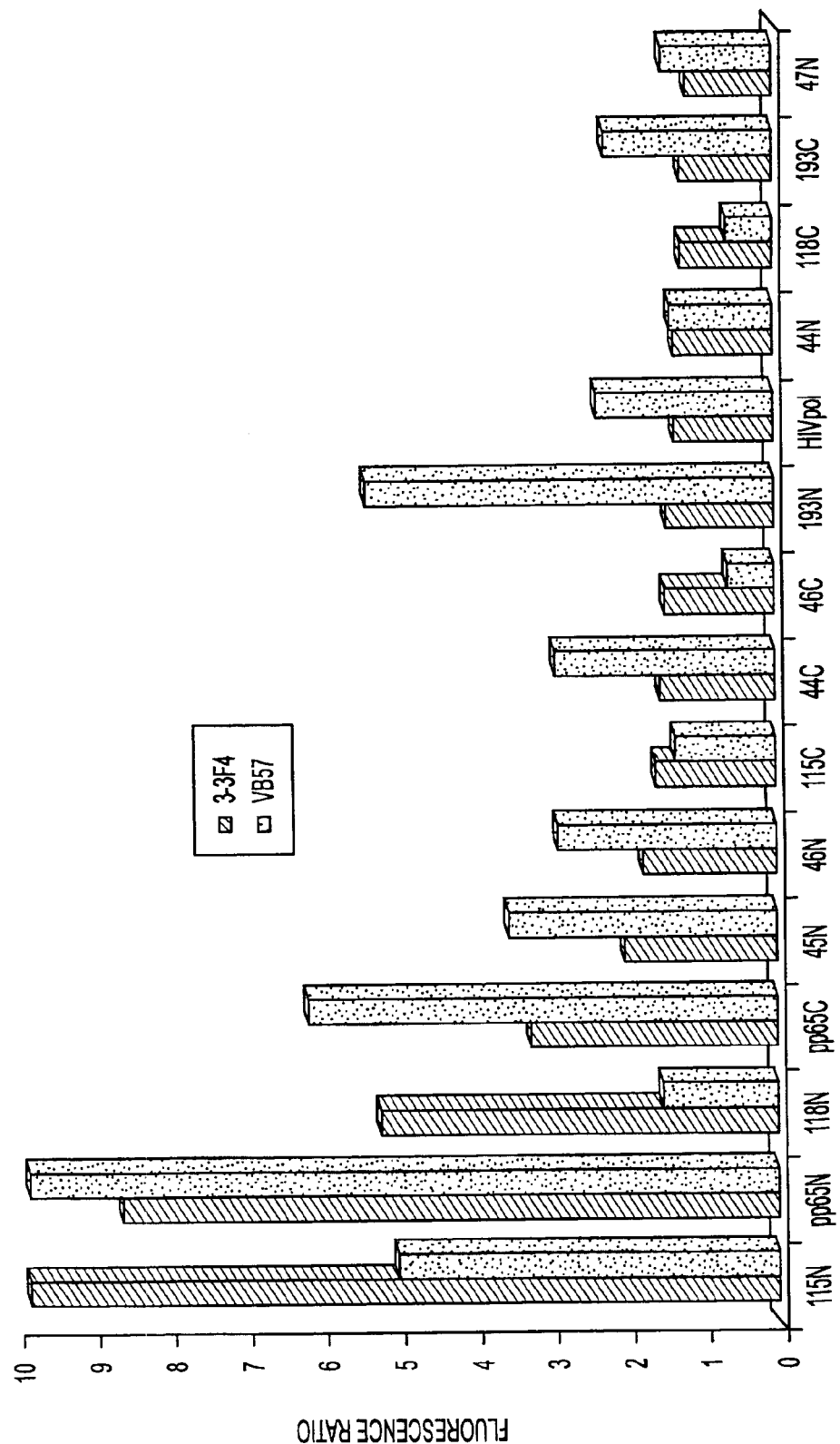
FIG. 4 is a bar graph showing specific fluorescence indicating binding of the indicated peptides to 3-3F4 and VB57.

T Cell Clone Flow-Cytometric Measurement of HLA-Ig Dimer Binding to T Cell Clone Mediated by Antigen Analog and Control Peptides HLA A2-Ig dimer aliquots were individually loaded with a series of peptides, and incubated with two different T cell clones, 3-3F4 and VB57. The soluble HLA-A2-Ig complexes (HLA dimers) were loaded with peptide according to the methods of Greten et al., *Proc. Natl. Acad. Sci. USA* 95:7568–7573 (1998). For each peptide analog to be tested, 10 μg of HLA dimers in 10 μl PBS containing 0.02% NaN$_3$ (Baker Chemical™, Phillipsburg, N.J.) was incubated for three days at 4° C. with 660-fold molar excess peptide. Dimers also were loaded with the pp65$_{495-503}$ native peptide, an irrelevant peptide (pp54 B*0702 epitope), and 2 µl PBS buffer containing 0.02% NaN$_3$, in all experiments to serve as controls. One microgram aliquots of peptide loaded dimers were mixed with 0.2 million of either T cell clone 3-3F4 or VB57 for 75 minutes on ice. Cells were washed in PBS containing 2% FBS and 0.02% NaN$_3$ (WB), and subsequently stained with 0.9 µl/sample of goat anti-mouse IgG$_1$-PE (Caltag™, Burlingame, Calif.). After two additional washings in WB, cells were analyzed by fluorescence-activated cell sorting (FACSCalibur™). Specific fluorescence was calculated as fluorescence ratio between the mean fluorescence of the peptide-loaded diners and the mean fluorescence of the buffer-loaded control diners. See FIG. 4. Peptides names ending in N are amidated, while those ending in C are free acids. Each peptide-loaded diner complex was tested at least twice with two different T cell clones (3-3F4 and VB57). The fluorescence indices indicated in the Figure are an average of both experiments. Measurements with both cell lines were normalized, so they could be displayed on the same axis.

Peptides 115 and 118, as well as the native sequence, pp65, bound well to 3-3F4, although 44, 46 and 193 were unexpectedly poor binders. VB57 had a similar binding profile, except that 118 was a poor binder, and 193 was among the better binders. Interestingly, the free acid forms of binding peptides 115, 118 and 193 (VB57 only) failed to bind to either T cell clone, in contrast to their amidated counterparts. The free acid 115, 118, and 193 peptides bound with similar affinity to the control C-terminal free acid peptide derived from HIV pol protein. The binding data indicates that mechanisms other than TCR or MHC binding may contribute to increased immunogenicity of these and other analog peptides.

Example 10

Recognition of the pp65$_{495-503}$ CTL Epitope by HLA A*0201 Donors

Figure 5A:
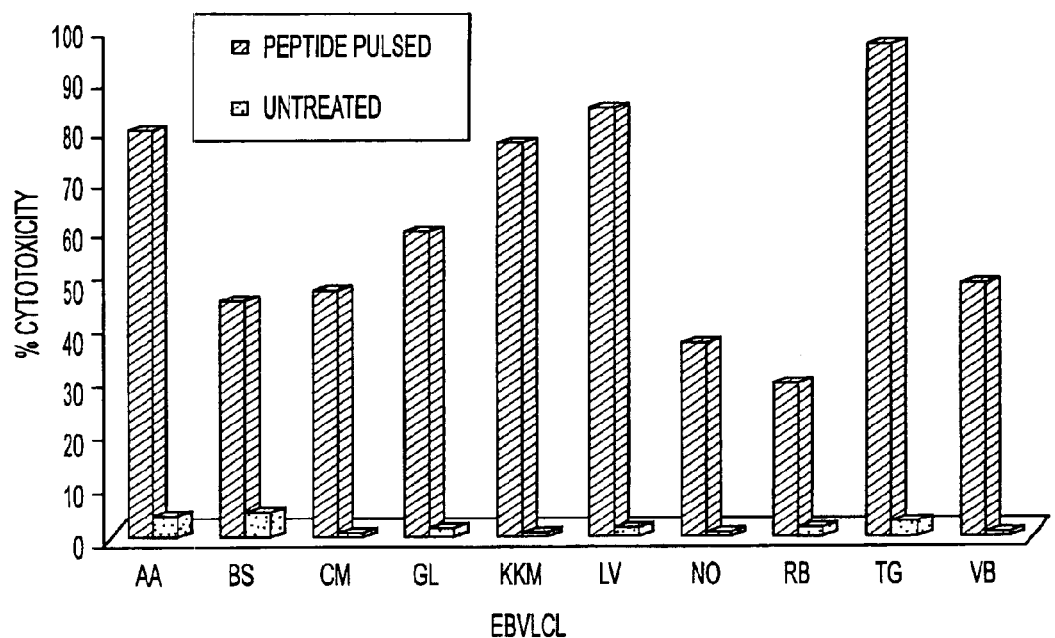
FIGS. 5A and 5B are a pair of bar graphs providing data regarding HCMV CTL epitope recognition by HCMV seropositive donors.
Figure 5B:
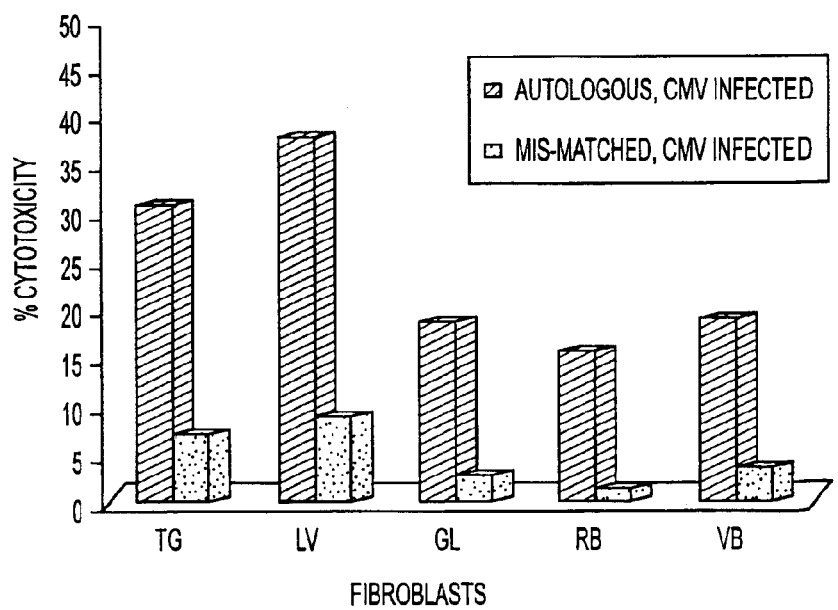
Figure 6A:
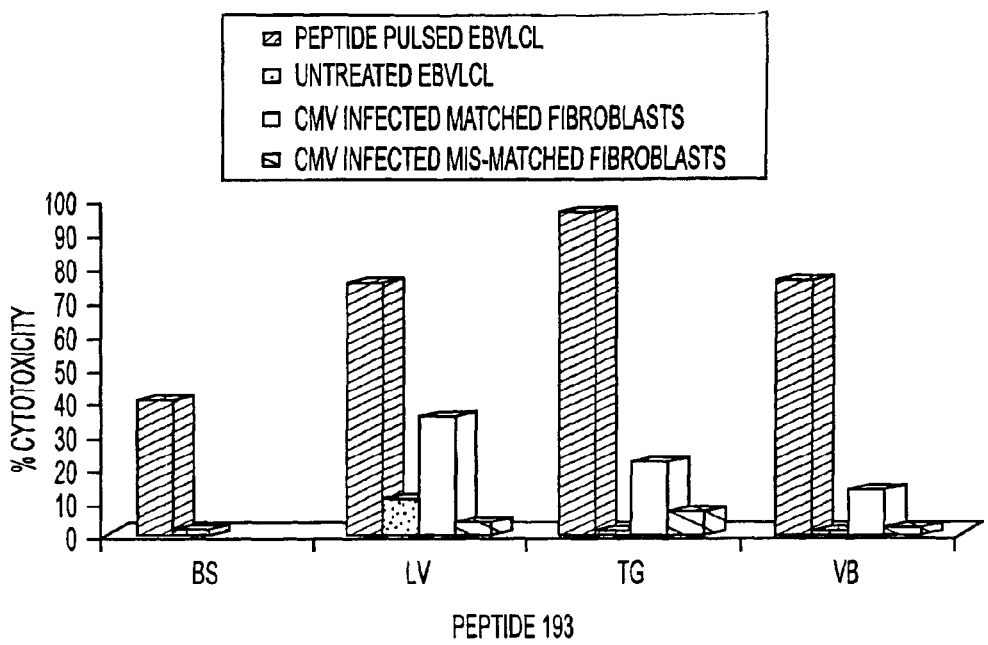
FIGS. 6A, 6B and 6C provide data regarding the recognition of three different CTL peptide analogs by HCMV seropositive donor CTL.
Figure 6B:
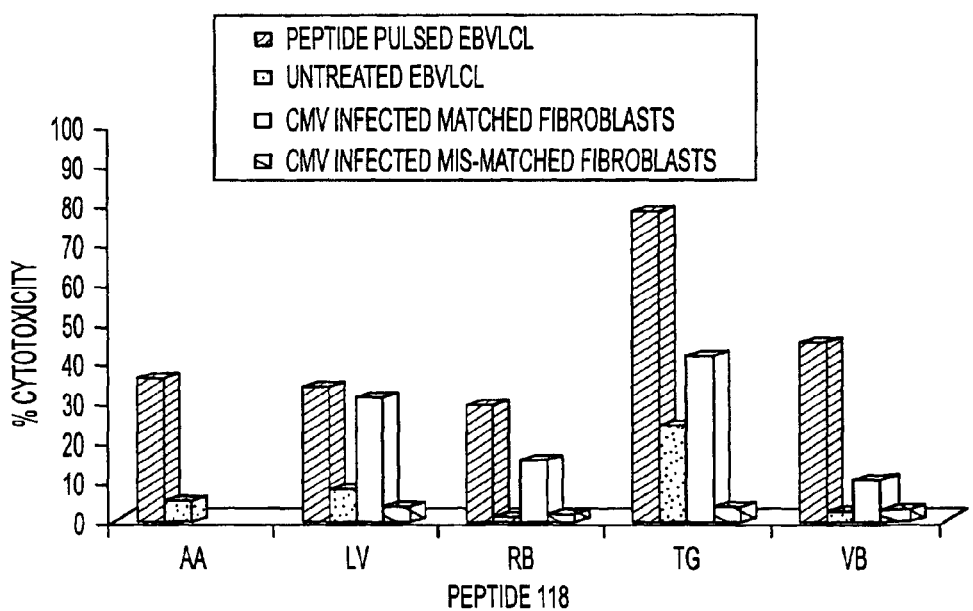
Figure 6C:
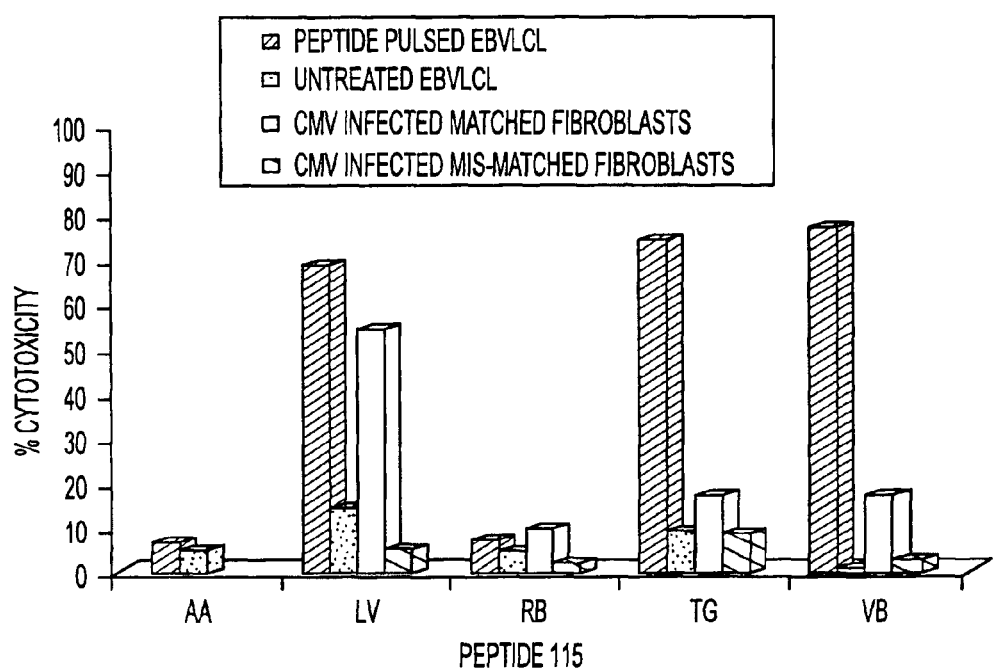

Ten randomly selected HCMV-seropositive, HLA A*0201+ healthy donors were selected for evaluation to confirm that the pp65$_{495-503}$ CTL epitope is widely recognized by HLA A*0201 persons. The haplotypes of examined individuals are shown in Table III. A one-step in vitro stimulation procedure modified from Lalvani et al., *J. Immunol. Meth.* 210:65–77 (1997), was carried out utilizing the pp65$_{495-503}$ CTL epitope (SEQ ID NO:1) as the immunogen. See LaRosa et al., *Blood* 92(10, Suppl. 1):518a (1998). In every case, the HLA A*0201 donors provoked a specific CTL response against T2 cells, and against HCMV-infected fibroblasts. See FIG. 5. AD169 strain HCMV was provided by J. Zaia (City of Hope Medical Center, COH). Virus stocks of 5–10 ×10$^6$ pfu/ml were prepared from the supernatant of infected MRCvhbm5 fibroblasts as previously described in Diamond et al., *Blood* 90:1751–1767 (1997) and used to infect dermal fibroblasts. Adherent cell lines were grown in fibroblast medium (FBM) consisting of D-MEM (Gibco™, Rockville, Md.) supplemented with 10% FBS (Hyclone™, Logan, Utah), 50 U/ml penicillin, 50 µg/ml streptomycin (Gibco™, Rockville, Md.) and 2 mM L-glutamine (Gibco™, Rockville, Md.). The results demonstrate that HCMV infection in HLA A*0201 positive healthy donors stimulates a specific immune response to SEQ ID NO:1 that is independent of haplotype, and likely to be universal in its expression.

TABLE III

Haplotypes of HCMV positive donors and TCR structure of T Cell Clone isolated from PBMC evaluated by IVS.

| Donor | HLA A1 | HLA A2 | HLA B1 | HLA B2 | TCC | TCRA | TCRB |
|---|---|---|---|---|---|---|---|
| AA | A2 | A2 | B44 | B60 | | | |
| BS | A2 | A26 | B51 | B62 | BS25 | AV2S1$_{A2}$-AJ45-AC | BV7S2A1-BJ2.1-BC2 |
| CM | A2 | A3 | B7 | B14 | | | |
| GL | A2 | A68 | B51 | B60 | 3-3F4 | AV18S2-AJ17.3-AC | |
| JE | A2 | A68 | B7 | N17 | | | |
| KKM | A2 | A1 | B27 | B44 | | | |
| LV | A2 | A2 | B51 | B55 | LVB | ND | ND |
| NO | A2 | A3 | B47 | B51 | | | |
| RB | A2 | A2 | B52 | B60 | | | |
| TG | A2 | A68 | B62 | B62 | TGA2 | AV3S1-AJ9.12-AC | BV13S2A1-BJ2.1-BC2 |
| VB | A2 | A3 | B44 | B62 | VB57 | AV18S1-AJ20-C | BV20S1A3-BJ1.1-BC1 |

Example 11

Enhanced Immunogenicity Peptide Analogs with Retained Universal Recognition

The PS-SCL library screen results pointed to two peptides (numbers 44N and 46N) recognized by the HLA A*0201-restricted T cell clone 3-3F4 with greater affinity than the native epitope. To test whether this increase in binding is common to all T cell clones which recognized the native epitope, a chromium release assay was performed using a cohort of four additional T cell clones derived from four different HCMV-seropositive volunteers and donor GL, from whom the clone 3-3F4 was obtained. Peptide analogs 44 and 46 were not recognized by any of the T cell clones in the cohort (data not shown).

To confirm that a T cell repertoire which recognizes peptides 44, 46 or both could be stimulated from a population of cells obtained from HCMV-seropositive individuals, the peripheral blood of four individuals was stimulated in vitro using peptides 44 and 46 (data not shown). Donor GL had cross-reactive T cells which were amplified by peptides 44 and 46, however, none of the other donors did.

To take advantage of the increased immunogenicity of peptides 44 and 46, while maintaining the universal recognition of the native peptide, library-directed changes were made to peptides 44 and 46, substituting back the native amino acids. A series of 21 peptides were constructed based upon the sequence of the tetra-substituted peptides 44 and 46 in each of the carboxyl terminal amidated and free acid forms. See Table IV. The peptides contained single, double, or triple substitutions of amino acids of the native sequence at the positions indicated. These peptides were assayed utilizing a standard chromium release assay with the screening T cell clone, 3-3F4, and a representative T cell clone (VB57) from another individual expressing a different T cell receptor.

Fifteen of the 21 amidated peptides were recognized by T cell clone 3-F4 at a lower concentration than the native epitope (Table II above), but only five were 100-fold or more active (Table IV). The free acid forms of the same peptide sequences were generally less potent. For example, peptide 193C (free acid) was approximately 100-fold less reactive than the native epitope, while peptide 193N (amide) was approximately 100-fold more immunogenic than the native epitope. Seven of the amidated peptides were recognized with a specific cytotoxicity of greater than 15% at a concentration of 0.05 nM, which is a greater sensitivity than the native epitope has for the same T cell clone. Only one of the free acid peptides was immunogenic below 0.05 nM, however. This peptide (111C) was equivalent to its amidated counterpart. See Table IV. These results further confirm that amidation of the carboxyl terminus of nonamer peptides provides greater flexibility for recognition.

TABLE IV

Substituted Carboxyl Terminal Amide and Free Acid Peptide Sequences Developed from Peptides 44 and 46.

| | Position | | | | | | | | | T Cell Clone | | | |
|---|---|---|---|---|---|---|---|---|---|---|---|---|---|
| | 1 | 2 | 3 | 4 | 5 | 6 | 7 | 8 | 9 | Amide | | Free Acid | |
| Peptide | | | | | | | A | | | | | | |
| Name; | N | | V | | | | T | T | | 3-3F4 | VB57 | 3-3F4 | VB57 |
| SEQ ID NO | Y | L | L | P | M | V | V | S | V | Peptide Concentration (nM) | | | |
| 193N; 37 | Y | L | V | P | M | V | A | T | V | 0.005 | 0.05 | >5 | >5 |
| 193C; 38 | | | | | | | | | | | | | |
| 194N; 39 | N | L | L | P | M | V | A | T | V | 0.05 | 0.5 | >5 | >5 |
| 194C; 40 | | | | | | | | | | | | | |
| 110N; 41 | N | L | V | P | M | V | V | T | V | 0.05 | >5 | 0.5 | ND |
| 110C; 42 | | | | | | | | | | | | | |
| 111N; 43 | N | L | V | P | M | V | T | T | V | 0.05 | >5 | 0.05 | 5 |
| 111C; 44 | | | | | | | | | | | | | |
| 112N; 45 | N | L | V | P | M | V | A | S | V | 0.5 | 0.5 | 5 | 0.5 |
| 112C; 46 | | | | | | | | | | | | | |
| 116N; 47 | N | L | L | P | M | V | V | T | V | 0.5 | >5 | >5 | ND |
| 116C; 48 | | | | | | | | | | | | | |
| 117N; 49 | N | L | L | P | M | V | T | T | V | 0.05 | >5 | 0.5 | 5 |
| 117C; 50 | | | | | | | | | | | | | |
| 118N; 51 | N | L | L | P | M | V | A | S | V | 0.05 | 0.05 | >5 | >5 |
| 118C; 52 | | | | | | | | | | | | | |
| 119N; 53 | N | L | V | P | M | V | V | S | V | 0.005 | >5 | >5 | >5 |
| 119C; 54 | | | | | | | | | | | | | |
| 120N; 55 | N | L | V | P | M | V | T | S | V | 0.05 | >5 | 5 | >5 |
| 120C; 56 | | | | | | | | | | | | | |
| 195N; 57 | Y | L | L | P | M | V | A | T | V | 0.005 | 0.5 | >5 | >5 |
| 195C; 58 | | | | | | | | | | | | | |
| 113N; 59 | Y | L | V | P | M | V | V | T | V | 0.5 | >5 | >5 | ND |
| 113C; 60 | | | | | | | | | | | | | |
| 114N; 61 | Y | L | V | P | M | V | T | T | V | 0.05 | 5 | 0.5 | 5 |
| 114C; 62 | | | | | | | | | | | | | |
| 115N; 63 | Y | L | V | P | M | V | A | S | V | 0.005 | 0.05 | >5 | 5 |
| 115C; 64 | | | | | | | | | | | | | |
| 126N; 65 | N | L | L | P | M | V | V | S | V | 0.005 | 0.5 | 5 | >5 |
| 126C; 66 | | | | | | | | | | | | | |
| 127N; 67 | N | L | L | P | M | V | T | S | V | 0.05 | >5 | 5 | >5 |
| 127C; 68 | | | | | | | | | | | | | |
| 124N; 69 | Y | L | V | P | M | V | V | S | V | 0.5 | 5 | >5 | >5 |
| 124C; 70 | | | | | | | | | | | | | |
| 125N; 71 | Y | L | V | P | M | V | T | S | V | 0.05 | >5 | >5 | >5 |
| 125C; 72 | | | | | | | | | | | | | |
| 121N; 73 | Y | L | L | P | M | V | V | T | V | 5 | >5 | >5 | ND |
| 121C; 74 | | | | | | | | | | | | | |
| 122N; 75 | Y | L | L | P | M | V | T | T | V | 5 | >5 | >5 | >5 |
| 122C; 76 | | | | | | | | | | | | | |
| 123N; 77 | Y | L | L | P | M | V | A | S | V | 0.05 | 0.5 | >5 | >5 |
| 123C; 78 | | | | | | | | | | | | | |

The amino acid substitutions that resulted in increased recognition by T cell clone 3-3F4 can be consolidated into a few categories. Most striking is the substitution of tyrosine for asparagine at position 1, which is present in three of the five most immunogenic peptides. Even as a single substitution it provides a 100-fold increase in reactivity compared to the native epitope. The substitution of serine at position 8 also is present in three of the five highest ranking peptides recognized by 3-3F4. There is no clear pattern within the 21 peptides, however, so it is not possible to predict which substitutions will be effective without screening all of the possible combinations.

T cell clone VB57, which expresses a different TCR than 3-3F4, evoked a different spectrum of responses (Table IV). Three peptide sequences (115N, 118N and 193N; SEQ ID NOS: 64, 52 and 38) are recognized with greater sensitivity by both T cell clones, and were considered candidate CTL epitope vaccines. These results demonstrate that it is possible to engineer peptides with enhanced recognition to multiple T cell clones.

The antigen analogs best recognized by both T cell clones 3-3F4 and VB57 (115N, 118N and 193N) were evaluated for recognition by a cohort of 3-3F4, VB57 and three additional T cell clones from three individuals. The T cell clones were stimulated in vitro with the native sequence of $pp65_{495-503}$ (SEQ ID NO:1) as described in Example 2. Limiting dilution cloning was conducted with a portion of the cells, and individual clones were evaluated using chromium release assays with the peptides indicated in Table V. The amount of peptide used to sensitize HLA A*0201-expressing EBVLCL target cells was 5.0 or 0.5 nM. Filled boxes indicate >30% specific cytotoxicity. Peptide 118 resulted in greater specific cytotoxicity at a lower concentration than the native sequence in three out of five T cell clones. Peptides 115 and 193 resulted in more potent lysis in two out of five T cell clones. For the best peptides, the sensitivity of T cell recognition is at least 10 times greater than the native epitope, although there were cases when the recognition is merely equivalent. These data confirm that these derived sequences were better recognized than the native CTL epitope, but still were recognized by a large number of T cell clones with differently expressed TCRs.

TABLE V

Recognition of Peptides by T Cell Clones from HLA A*0201 Individuals Seropositive for HHCMV.

| | Native sequence | | Peptide 115 | | Peptide 118 | | Peptide 193 | |
|---|---|---|---|---|---|---|---|---|
| T Cell Clone | 5.0 nM | 0.5 nM | 5.0 nM | 0.5 nM | 5.0 nM | 0.5 nM | 5.0 nM | 0.5 nM |
| GL 3-3F7 | | | | | | | | |
| VB 57 | | | | | | | | |
| BS 25 | | | | | | | | |
| LV B | | | | | | | | |
| TG 2 | | | | | | | | |

Example 12

Recognition of Antigen Analogs by Multiple T Cell Clones

Peripheral blood from separate individuals was stimulated with peptides 115, 118, and 193 and subjected to a chromium release assay. Aliquots of magnetically-depleted lymphocytes were incubated with autologous antigen presenting cells loaded with one of four amidated peptides (SEQ ID NO:1; results not shown) under in vitro stimulation conditions as described above. Lymphocytes from three individuals were used for all four peptides, including SEQ ID NO:1, and one individual (BS) was evaluated with 193 peptide and the positive control. T cell clones from three individuals vigorously responded to the in vitro stimulation conducted with all three peptides. See FIG. 6. Peptides 118 and 193 were recognized by all evaluated individuals, whereas peptide 115 was recognized in three out of five individuals. Effector cells from the cultures of three individuals specifically recognized HCMV-infected fibroblasts after stimulation by all three peptides.

Example 13

MHC Binding Affinity of Antigen Analogs by T2 Assembly Assay.

Five analog peptides and the native sequence were evaluated for affinity to HLA A*0201 as both free acids and amides by T2 assembly assay. See the methods of Nijman et al., *Eur. J. Immunol.* 23:1215–1219 (1993). A known HLA A*0201 binding peptide served as control.

T2 cells, which express HLA-A*0201 molecules, were cultured in IMDM (Gibco™, Rockville, Md.) with supplements as described for EBVLCL. For each analog to be tested, 250,000 T2 cells were washed twice and resuspended in serum free IMDM and incubated overnight with 100 μM peptide together with 15 μg/ml human $\beta_2$-microglobulin (Sigma™, Lt. Louis, Mo.) at 37° C. in a 5% $CO_2$ incubator. Peptide loaded cells were washed once at 4° C. with cold PBS containing 0.05% BSA (Sigma™, St.; Louis, Mo.) and 0.02% $NaN_3$ followed by incubation with 1 μg/sample murine mAb BB7.2, an antibody specific for cell-surface HLA A*0201 (ATCC), for 30 minutes at 4° C. After washing twice with cold buffer, FITC-conjugated rat anti-mouse IgG$_{2a/2b}$ (1:40 dilution; Pharmingen™, San Diego, Calif.) was added and incubated for another 30 minutes at 4° C. The cells were washed twice in cold buffer, and mean fluorescence intensity (MFI) of $10^4$ gated cells was measured using a FACSCalibur™.

Figure 7:
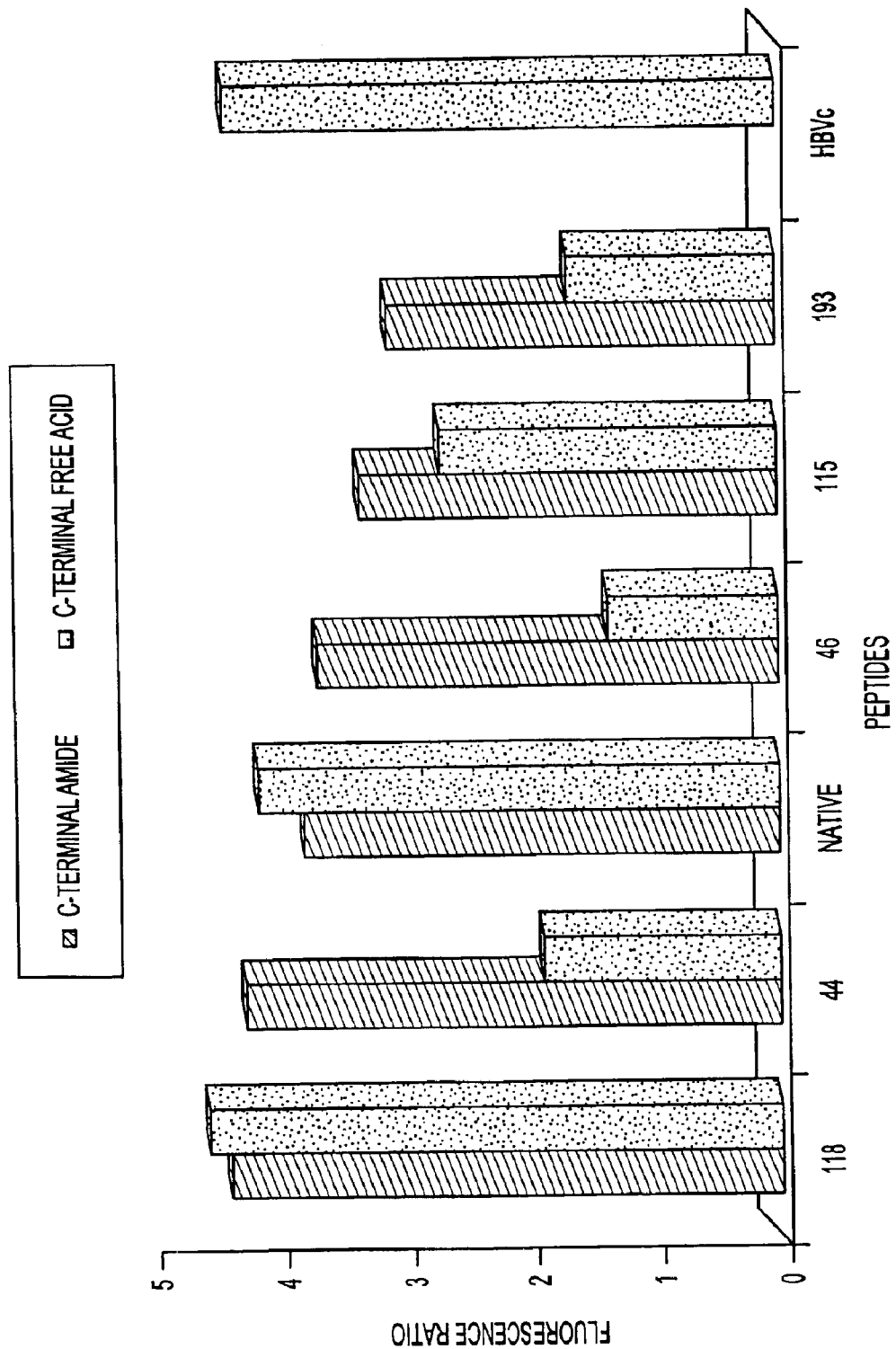
FIG. 7 is a bar graph showing the results of a T2 assembly assay.

Representative results from three separate measurements are shown in FIG. 7. Fluorescence ratio is defined as mean fluorescence with peptide/mean fluorescence without peptide. Results for the amidated peptides indicate only slight changes in MHC binding. Ranking amidated peptides according to strength of MHC binding does not reveal a pattern that would explain the restricted recognition of peptides 44 and 46 versus the native sequence. Although peptides 44 and 46 have been shown to be strongly immunogenic to T cell clone 3-3F4, their MHC affinity measured by this assay is not dramatically different from the native sequence. This indicates that the reason for the enhanced immunogenicity of these two peptides does not relate to affinity to HLA Class I.

What is claimed is:

1. A vaccine against human cytomogalovirus which comprises a peptide selected from the group consisting of SEQ ID NOs: 38, 52 and 64.

2. A vaccine of claim 1 which further comprises an adjuvant.

3. A vaccine of claim 2 wherein said adjuvant is a DNA adjuvant.

4. A vaccine of claim 3, wherein said DNA adjuvant is a CpG DNA adjuvant.

5. An immunogenic composition for modifying the immune response of a mammal to human cytomegalovirus which comprises a peptide selected from the group consisting of SEQ ID Nos: 38, 52 and 64.

6. An immunogenic composition of claim 5 which further comprises an adjuvant.

7. An immunogenic composition of claim 6 wherein said adjuvant is a DNA adjuvant.

8. An immunogenic composition of claim 7 wherein said DNA adjuvant is a CpG DNA adjuvant.

* * * * *

UNITED STATES PATENT AND TRADEMARK OFFICE
CERTIFICATE OF CORRECTION

PATENT NO. : 6,951,651 B2
APPLICATION NO. : 10/643888
DATED : October 4, 2005
INVENTOR(S) : Don J. Diamond It is certified that error appears in the above-identified patent and that said Letters Patent is hereby corrected as shown below:

On the Title Page, Item (56) References Cited, col. 2, line 1, "Zala" should read -- Zaia --.

On page 2, col. 1, line 34, "Larosa" should read -- LaRosa --.

On page 3, col. 2, under "OTHER PUBLICATIONS," add the following references:

-- Altman, John D., et al., "Phenotypic Analysis of Antigen-Specific T Lymphocytes," Science 274:94-96, October 4, 1996.

Boppana, Suresh B., et al., "Recognition of Human Cytomegalovirus Gene Products by HCMV-Specific Cytotoxic T Cells," Virology 222 (Article 0424) :293-296, 1996.

BenMohamed, Lbachir, et al., "Induction of CTL Response by a Minimal Epitope Vaccine in HLA A*0201/DR1 Transgenic Mice: Dependence on HLA Class II Restricted $T_H$ Response," Human Immunology 61:764-779, 2000.

Clave, Emmanuel, et al., "Use of a CMV pp65-Specific HLA Tetramer to Select and Expand CMV-Specific CD8+ CTL," Abstract #679, Post Board #-Session 679-1, Blood 94 (10 Suppl. 1) :155a, Noember 15, 1999.

Pande, Hema, et al., "Cloning and physical mapping of a gene fragment coding for a 64-kilodalton major late antigen of human cytomegalovirus," Proc. Natl. Acad. Sci USA 81:4965-4969, August 1984.

Spaete, Richard R. et al., "Human Cytomegalovirus Strain Towne Glycoprotein B is Processed by Proteolytic Cleavage," Virology 167:207-225, 1988. --

On col. 1, line 6, "tiled" should read -- filed --.

On col. 7, line 30, "XXXXXXO$_7$, XX" should read -- XXXXXXO$_7$XX --.

On col. 13, line 41, "p65495-503" should read -- pp65$_{495\text{-}503}$ --.

On col. 14, line 27, delete -- Dynabead --.

UNITED STATES PATENT AND TRADEMARK OFFICE
CERTIFICATE OF CORRECTION

PATENT NO.        : 6,951,651 B2
APPLICATION NO. : 10/643888
DATED             : October 4, 2005
INVENTOR(S)       : Don J. Diamond It is certified that error appears in the above-identified patent and that said Letters Patent is hereby corrected as shown below:

On col. 25, delete Table V and replace with the following table:

TABLE V
Recognition of Peptides by T Cell Clones from HLA A* 0201 Individuals Seropositive for HHCMV

| T Cell Clone | Native sequence 5.0 nM | Native sequence 0.5 nM | Peptide 115 5.0 nM | Peptide 115 0.5 nM | Peptide 118 5.0 nM | Peptide 118 0.5 nM | Peptide 193 5.0 nM | Peptide 193 0.5 nM |
|---|---|---|---|---|---|---|---|---|
| GL 3-3F7 | X |   | X | X | X | X | X | X |
| VB 57 | X |   | X | X | X | X | X | X |
| BS 25 | X |   |   |   | X | X |   |   |
| LV B | X |   |   |   |   |   | X |   |
| TG 2 | X |   |   |   | X |   |   |   |

Signed and Sealed this

Tenth Day of October, 2006

JON W. DUDAS
*Director of the United States Patent and Trademark Office*

SEQUENCE LISTING

```
<160> NUMBER OF SEQ ID NOS: 78

<210> SEQ ID NO 1
<211> LENGTH: 9
<212> TYPE: PRT
<213> ORGANISM: Human cytomegalovirus

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 2

Tyr Leu Leu Pro Met Val Val Ser Val
1               5

<210> SEQ ID NO 3
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 3

Tyr Leu Leu Pro Met Val Thr Ser Val
1               5

<210> SEQ ID NO 4
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 4

Ala Leu Val Pro Met Val Ala Thr Val
1               5

<210> SEQ ID NO 5
```

```
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 5

Asn Ala Val Pro Met Val Ala Thr Val
1               5

<210> SEQ ID NO 6
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 6

Asn Leu Ala Pro Met Val Ala Thr Val
1               5

<210> SEQ ID NO 7
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 7

Asn Leu Val Ala Met Val Ala Thr Val
1               5

<210> SEQ ID NO 8
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 8

Asn Leu Val Pro Ala Val Ala Thr Val
1               5

<210> SEQ ID NO 9
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 9

Asn Leu Val Pro Met Ala Ala Thr Val
1               5

<210> SEQ ID NO 10
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 10

Asn Leu Val Pro Met Val Ala Ala Val
1               5

<210> SEQ ID NO 11
<211> LENGTH: 9
```

```
<212> TYPE: PRT
<213> ORGANISM: Artificial Sequence
<220> FEATURE:
<223> OTHER INFORMATION: HCMV vaccine peptide

<400> SEQUENCE: 11

Asn Leu Val Pro Met Val Ala Thr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 12

Ala Leu Val Pro Met Val Ala Thr Val
1               5

<210> SEQ ID NO 13
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 13

Asn Ala Val Pro Met Val Ala Thr Val
1               5

<210> SEQ ID NO 14
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 14

Asn Leu Ala Pro Met Val Ala Thr Val
1               5

<210> SEQ ID NO 15
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 15

Asn Leu Val Ala Met Val Ala Thr Val
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 16

Asn Leu Val Pro Ala Val Ala Thr Val
1               5

<210> SEQ ID NO 17
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 17

Asn Leu Val Pro Met Ala Ala Thr Val
1               5

<210> SEQ ID NO 18
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 18

Asn Leu Val Pro Met Val Ala Thr Val
1               5

<210> SEQ ID NO 19
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 19

Asn Leu Val Pro Met Val Ala Ala Val
1               5

<210> SEQ ID NO 20
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION
```

```
<400> SEQUENCE: 20

Asn Leu Val Pro Met Val Ala Thr Ala
1               5

<210> SEQ ID NO 21
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 21

Tyr Leu Leu Trp Met Val Thr Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 22

Tyr Leu Leu Trp Tyr Val Val Ser Val
1               5

<210> SEQ ID NO 23
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 23

Tyr Leu Leu Pro Met Val Thr Pro Val
1               5

<210> SEQ ID NO 24
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 24

Tyr Leu Leu Trp Met Val Val Ser Val
1               5

<210> SEQ ID NO 25
<211> LENGTH: 9
<212> TYPE: PRT
<213> ORGANISM: Artificial Sequence
<220> FEATURE:
```

```
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 25

Tyr Leu Leu Trp Met Val Val Pro Val
1               5

<210> SEQ ID NO 26
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 26

Tyr Leu Leu Trp Met Val Thr Pro Val
1               5

<210> SEQ ID NO 27
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 27

Tyr Leu Leu Trp Tyr Val Thr Ser Val
1               5

<210> SEQ ID NO 28
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 28

Tyr Leu Leu Pro Met Val Val Pro Val
1               5

<210> SEQ ID NO 29
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 29

Tyr Leu Leu Pro Tyr Val Val Ser Val
1               5
```

```
<210> SEQ ID NO 30
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 30

Tyr Leu Leu Pro Tyr Val Val Pro Val
 1               5

<210> SEQ ID NO 31
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 31

Tyr Leu Leu Pro Tyr Val Thr Ser Val
 1               5

<210> SEQ ID NO 32
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 32

Tyr Leu Leu Pro Tyr Val Thr Pro Val
 1               5

<210> SEQ ID NO 33
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 33

Tyr Leu Leu Trp Tyr Val Val Pro Val
 1               5

<210> SEQ ID NO 34
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION
```

```
<400> SEQUENCE: 34

Tyr Leu Leu Trp Tyr Val Thr Pro Val
1               5

<210> SEQ ID NO 35
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 35

Tyr Leu Leu Pro Met Val Val Ser Val
1               5

<210> SEQ ID NO 36
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 36

Tyr Leu Leu Pro Met Val Thr Ser Val
1               5

<210> SEQ ID NO 37
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 37

Tyr Leu Val Pro Met Val Ala Thr Val
1               5

<210> SEQ ID NO 38
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 38

Tyr Leu Val Pro Met Val Ala Thr Val
1               5

<210> SEQ ID NO 39
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 39

Asn Leu Leu Pro Met Val Ala Thr Val
1               5
```

-continued

```
<210> SEQ ID NO 40
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 40

Asn Leu Leu Pro Met Val Ala Thr Val
1               5

<210> SEQ ID NO 41
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 41

Asn Leu Val Pro Met Val Val Thr Val
1               5

<210> SEQ ID NO 42
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 42

Asn Leu Val Pro Met Val Val Thr Val
1               5

<210> SEQ ID NO 43
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 43

Asn Leu Val Pro Met Val Thr Thr Val
1               5

<210> SEQ ID NO 44
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 44

Asn Leu Val Pro Met Val Thr Thr Val
1               5

<210> SEQ ID NO 45
<211> LENGTH: 9
<212> TYPE: PRT
<213> ORGANISM: Artificial Sequence
<220> FEATURE:
```

```
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 45

Asn Leu Val Pro Met Val Ala Ser Val
1               5

<210> SEQ ID NO 46
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 46

Asn Leu Val Pro Met Val Ala Ser Val
1               5

<210> SEQ ID NO 47
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 47

Asn Leu Leu Pro Met Val Val Thr Val
1               5

<210> SEQ ID NO 48
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 48

Asn Leu Leu Pro Met Val Val Thr Val
1               5

<210> SEQ ID NO 49
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 49

Asn Leu Leu Pro Met Val Thr Thr Val
1               5

<210> SEQ ID NO 50
<211> LENGTH: 9
<212> TYPE: PRT
<213> ORGANISM: Artificial Sequence
<220> FEATURE:
<223> OTHER INFORMATION: HCMV vaccine peptide
```

-continued

```
<400> SEQUENCE: 50

Asn Leu Leu Pro Met Val Thr Thr Val
1               5

<210> SEQ ID NO 51
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 51

Asn Leu Leu Pro Met Val Ala Ser Val
1               5

<210> SEQ ID NO 52
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 52

Asn Leu Leu Pro Met Val Ala Ser Val
1               5

<210> SEQ ID NO 53
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 53

Asn Leu Val Pro Met Val Val Ser Val
1               5

<210> SEQ ID NO 54
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 54

Asn Leu Val Pro Met Val Val Ser Val
1               5

<210> SEQ ID NO 55
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 55
```

```
Asn Leu Val Pro Met Val Thr Ser Val
1               5

<210> SEQ ID NO 56
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 56

Asn Leu Val Pro Met Val Thr Ser Val
1               5

<210> SEQ ID NO 57
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 57

Tyr Leu Leu Pro Met Val Ala Thr Val
1               5

<210> SEQ ID NO 58
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 58

Tyr Leu Leu Pro Met Val Ala Thr Val
1               5

<210> SEQ ID NO 59
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 59

Tyr Leu Val Pro Met Val Val Thr Val
1               5

<210> SEQ ID NO 60
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 60

Tyr Leu Val Pro Met Val Val Thr Val
1               5

<210> SEQ ID NO 61
<211> LENGTH: 9
```

```
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 61

Tyr Leu Val Pro Met Val Thr Thr Val
1               5

<210> SEQ ID NO 62
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 62

Tyr Leu Val Pro Met Val Thr Thr Val
1               5

<210> SEQ ID NO 63
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 63

Tyr Leu Val Pro Met Val Ala Ser Val
1               5

<210> SEQ ID NO 64
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 64

Tyr Leu Val Pro Met Val Ala Ser Val
1               5

<210> SEQ ID NO 65
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 65

Asn Leu Leu Pro Met Val Val Ser Val
1               5

<210> SEQ ID NO 66
<211> LENGTH: 9
<212> TYPE: PRT
<213> ORGANISM: Artificial Sequence
```

```
<220> FEATURE:
<223> OTHER INFORMATION: HCMV vaccine peptide

<400> SEQUENCE: 66

Asn Leu Leu Pro Met Val Val Ser Val
1               5

<210> SEQ ID NO 67
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 67

Asn Leu Leu Pro Met Val Thr Ser Val
1               5

<210> SEQ ID NO 68
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 68

Asn Leu Leu Pro Met Val Thr Ser Val
1               5

<210> SEQ ID NO 69
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 69

Tyr Leu Val Pro Met Val Val Ser Val
1               5

<210> SEQ ID NO 70
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 70

Tyr Leu Val Pro Met Val Val Ser Val
1               5

<210> SEQ ID NO 71
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION
```

```
<400> SEQUENCE: 71

Tyr Leu Val Pro Met Val Thr Ser Val
1               5

<210> SEQ ID NO 72
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 72

Tyr Leu Val Pro Met Val Thr Ser Val
1               5

<210> SEQ ID NO 73
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 73

Tyr Leu Leu Pro Met Val Val Thr Val
1               5

<210> SEQ ID NO 74
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 74

Tyr Leu Leu Pro Met Val Val Thr Val
1               5

<210> SEQ ID NO 75
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 75

Tyr Leu Leu Pro Met Val Thr Thr Val
1               5

<210> SEQ ID NO 76
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 76

Tyr Leu Leu Pro Met Val Thr Thr Val
1               5
```

```
<210> SEQ ID NO 77
<211> LENGTH: 9
<212> TYPE: PRT
<213> ORGANISM: Artificial Sequence
<220> FEATURE:
<223> OTHER INFORMATION: HCMV vaccine peptide
<220> FEATURE:
<221> NAME/KEY: MOD_RES
<222> LOCATION: (9)..(9)
<223> OTHER INFORMATION: AMIDATION

<400> SEQUENCE: 77

Tyr Leu Leu Pro Met Val Ala Ser Val
1               5

<210> SEQ ID NO 78
<211> LENGTH: 9
<212> TYPE: PRT
<213> ORGANISM: Artificial Sequence
<220> FEATURE:
<223> OTHER INFORMATION: HCMV vaccine peptide

<400> SEQUENCE: 78

Tyr Leu Leu Pro Met Val Ala Ser Val
1               5
```